(12) United States Patent
Papautsky et al.

(10) Patent No.: US 8,208,138 B2
(45) Date of Patent: Jun. 26, 2012

(54) SPIRAL MICROCHANNEL PARTICLE SEPARATORS, STRAIGHT MICROCHANNEL PARTICLE SEPARATORS, AND CONTINUOUS PARTICLE SEPARATOR AND DETECTOR SYSTEMS

(75) Inventors: Ian Papautsky, Mason, OH (US); Ali Asgar S. Bhagat, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 59 days.

(21) Appl. No.: 12/890,580

(22) Filed: Sep. 24, 2010

(65) Prior Publication Data
US 2011/0096327 A1    Apr. 28, 2011

Related U.S. Application Data

(60) Provisional application No. 61/245,518, filed on Sep. 24, 2009.

(51) Int. Cl.
*G01N 15/02*    (2006.01)

(52) U.S. Cl. ........................................ 356/335; 356/336

(58) Field of Classification Search .......... 356/335–343; 209/132–134
See application file for complete search history.

(56) References Cited

U.S. PATENT DOCUMENTS
2009/0014360 A1* 1/2009 Toner et al. .................... 209/208

OTHER PUBLICATIONS

A. A. S. Bhagat, Kuntaegowdanahalli SS, Papautsky I (2008) Continuous particle separation in spiral microchannels using dean flows and differential migration. Lab Chip 8:1906.
A. A. S. Bhagat, Pais A, Jothimuthu P, Papautsky I (2007b) Re-usable quick-release interconnect for characterization of microfluidic systems. J Micromech Microeng 17:42-49.
A. A. S. Bhagat, Papautsky I (2008) Enhancing particle dispersion in a passive planar micromixer using rectangular obstacles. J Micromech Microeng 18:085005.
A. A. S. Bhagat, Peterson ETK, Papautsky I (2007a) A passive planar micromixer with obstructions for mixing at low Reynolds numbers. J Micromech Microeng 17:1017-1024.
A. A. S. Bhagat, S. S. Kuntaegowdanahalli and I. Papautsky, Microfluid. Nanofluid., DOI: 10.1007/s10404-008-0377-2.
A. A. S. Bhagat, S. S. Kuntaegowdanahalli and I. Papautsky, Phys. Fluids, 2008, 20, 101702.
A. Nilsson, Petersson F, Jonsson H et al (2004) Acoustic control of suspended particles in micro fluidic chips. Lab Chip 4:131-135.
A. Seaton, Donaldson K (2005) Nanoscience, nanotoxicology, and the need to think small. Lancet 365:923-924.

(Continued)

*Primary Examiner* — Tri T Ton
(74) *Attorney, Agent, or Firm* — Dinsmore & Shohl LLP

(57) ABSTRACT

A spiral microchannel particle separator includes an inlet for receiving a solution containing particles, at least two outlets, and a microchannel arranged in a plurality of loops. Particles within a solution flowing through the spiral microchannel experience a lift force $F_L$ and a Dean drag force $F_D$. The spiral radius of curvature R and the hydraulic diameter $D_h$ of the spiral microchannel are such that for a flow rate U of the solution, the lift force $F_L$ and a Dean drag force $F_D$ are approximately equal and act in opposite directions for particles of a first size. The particles of the first size are focused in a single stream located at an equilibrium position near an inner wall of the microchannel. In another embodiment, a straight microchannel particle separator separates particles by modulating shear rates via high aspect ratios that focuses particles of a first size along two first walls.

18 Claims, 22 Drawing Sheets

OTHER PUBLICATIONS

A. Y. Fu, C. Spence, A. Scherer, F. H. Arnold and S. R. Quake, Nature Biotech., 1999, 17, 1109-1111.
B. Chun, Ladd AJC (2006) Inertial migration of neutrally buoyant: particles in a square duct: an investigation of multiple equilibrium positions. Phys Fluids 18:031704.
B. Gale, K. Caldwell, and A. B. Frazier, "Geometric scaling effects in electrical field flow fractionation. 2. Experimental results," Anal. Chem. 74, 1024__2002__.
C. B. Fuh, Giddings JC (1997) Separation of submicron pharmaceutical emulsions with centrifugal split-flow thin (SPLITT) fractionation. J Microcolumn Sep 9:205-211.
C. Blattert, R. Jurischka, A. Schoth, P. Kerth and W. Menz, Proc SPIE, 2004, 5345, 17-25.
D. Di Carlo, Irimia D, Tompkins RG et al (2007) Continuous inertial focusing, ordering, and separation of particles in microchannels. PNAS 104:18892-18897.
D. Di Carlo, J. F. Edd, D. Irimia, R. G. Tompkins and M. Toner, Anal. Chem., 2008, 80, 2204-2211.
D. Shi, N. H. El-Farra, M. Li, P. Mhaskar and P. D. Christofides, Chem. Eng. Sci., 2006, 61, 268-281.
D. W. Inglis, J. A. Davis, R. H. Austin and J. C. Sturm, Lab Chip, 2006, 6, 655-658.
E. Chmela, Tijssen R, Blom MT et al (2002) A chip system for size separation of macromolecules and particles by hydrodynamic chromatography. Anal Chem 74:3470-3475.
E. Hedlund, J. Pruszak, A. Ferree, A. Vinuela, S. Hong, O. Isacson and K S. Kim, Stem Cells, 2007, 25, 1126-35.
E. S. Asmolov (1999) The inertial lift on a spherical particle in a plane Poiseuille flow at large channel Reynolds number. J Fluid Mech 381:63-87.
F.-K. Liu, Y.-Y. Lin and C.-H. Wu, Anal. Chim. Acta, 2005, 528, 249-254.
G. Blankenstein, Larsen UD (1998) Modular concept of a laboratory on a chip for chemical and biochemical analysis. Biosens Bioelectron 13:427-438.
G. Segre and A. Silberberg, "Behaviour of macroscopic rigid spheres in Poiseuille flow," J. Fluid Mech. 14, 136__1962__.
G. Segre and A. Silberberg, "Radial particle displacements in Poiseuille flow of suspensions," Nature__London__189, 209__1961__.
G.-T. Wei, F.-K. Liu, and C. Wang, "Shape separation of nanometer gold particles by size-exclusion chromatography," Anal. Chem. 71, 2085__1999__.
H. Odegaard (1998) Optimised particle separation in the primary step of wastewater treatment. Water Sci Technol 37:43-53.
I. Gregoratto, C. J. McNeil and M. W. Reeks, Proc. SPIE, 2007, 6465, 646503.
J. C. Giddings, "Field-flow fractionation: Analysis of macromolecular, colloidal, and particulate materials," Science 260, 1456__1993__.
J. P. Beech and J. O. Tegenfeldt, Lab Chip, 2008, 8, 657-659.
J. P. Brody and P. Yager, Sens. Actuators, A, 1997, 58, 13-18.
J. Seo, M. H. Lean and A. Kole, Appl. Phys. Lett., 2007, 91, 033901.
J. Seo, M. H. Lean and A. Kole, J. Chromatogr. A, 2007, 1162, 126-131.
J. Takagi, M. Yamada, M. Yasuda and M. Seki, Lab Chip, 2005, 5, 778-784.
J.-P. Matas, Glezer V, Guazzelli E, Morris JF (2004c) Trains of particles in finite-Reynolds-number pipe flow. Phys Fluids 16:4192-4195.
J-P. Matas, J. Morris, and E. Guazzelli, "Inertial migration of rigid spherical particles in Poiseuille flow," J. Fluid Mech. 515, 171__2004__.
J.-P. Matas, J. Morris, and E. Guazzelli, "Lateral forces on a sphere," Oil Gas Sci. Technol. 59, 59__2004__.
K. Thomas, Sayre P (2005) Research strategies for safety evaluation of nanomaterials. Part I. Evaluating the human health implications of exposure to nanoscale materials. Toxicol Sci 87:316-321.
L. B. Leverette, Hellums JD, Alfrey CP, Lynch EC (1972) Red blood cell damage by shear stress. Biophys J 12:257-273.
L. R. Huang, E. C. Cox, R. H. Austin and J. C. Sturm, Science, 2004, 304, 987-990.
M. Durr, J. Kentsch, T. Muller, T. Schnelle, and M. Stelzle, "Microdevices for manipulation and accumulation of micro-and nanoparticles by dielectrophoresis," Electrophoresis 24, 72__2003__.
M. Kersaudy-Kerhoas, R. Dhariwal and M. P. Y. Desmulliez, IET Nanobiotechnol., 2008, 2, 1-13.
M. T. Blom, E. Chmela, R. E. Oosterbroek, R. Tijssen and A. Van Den Berg, Anal. Chem., 2003, 75, 6761-6768.
M. Tachibana, "On the behaviour of a sphere in the laminar tube flows," Rheol. Acta 12, 58__1973__.
M. Toner and D. Irimia, Annu. Rev. Biomed. Eng., 2005, 7, 77-103.
M. Yamada, Nakashima M, Seki M (2004) Pinched flow fractionation—continuous size separation of particles utilizing a laminar flow profile in a pinched microchannel. Anal Chem 76:5465-5471.
N. Callens, Hoyos M, Kurowski P, Iorio CS (2008) Particle sorting in a mini step-split-flow thin channel: influence of hydrodynamic shear on transversal migration. Anal Chem 80:4866-4875.
N. Pamme, "Continuous flow separations in microfluidic devices," Lab Chip 7, 1644__2007__.
P. Jandik, B. H. Weigl, N. Kessler, J. Cheng, C. J. Morris, T. Schulte and N. Avdalovic, J. Chromatogr., A, 2002, 954, 33-40.
R. E. Hampton, Mammoli AA, Graham AL, Tetlow N, Altobelli SA (1997) Migration of particles undergoing pressure-driven flow in a circular conduit. J Rheol 41:621-640.
R. Eichhorn and S. Small, J. Fluid Mech., 1964, 20, 513-527.
S. Ookawara, D. Street and K. Ogawa, Chem. Eng. Sci., 2006, 61, 3714-3724.
S. Ookawara, R. Higashi, D. Street and K. Ogawa, Chem. Eng. J., 2004, 101, 171-178.
T. D. Chung and H. C. Kim, Electrophoresis, 2007, 28, 4511-4520. ART__B908271A.
T. L. Edwards, B. K. Gale and A. B. Frazier, Anal. Chem., 2002, 74, 1211-1216.
W. Inglis, J. A. Davis, R. H. Austin and J. C. Sturm, Lab Chip, 2006, 6, 655-658.
W. R. Dean, Phil. Mag. Ser. 7, 1927, 4, 208-223.
W. R. Dean, Phil. Mag. Ser. 7, 1928, 5, 673-695.
W.-M. Hwang, C.-Y. Lee, D. W. Boo, and J.-G. Choi, "Separation of nanoparticles in different sizes and compositions by capillary electrophoresis," Bull. Korean Chem. Soc. 24, 684__2003__.
X. Xu, K. K. Caswell, E. Tucker, S. Kabisatpathy, K. L. Brodhacker and W. A. Scrivens, J. Chromatogr. A, 2007, 1167, 35-41.
Y. Kim and J. Yoo, "The lateral migration of neutrally-buoyant spheres transported through square microchannels," J. Micromech. Microeng. 18, 065015__2008__.
Z. Wu, K. Hjort, G. Wicher and A. Fex Svenningsen, Biomed. Microdevices, 2008, 10, 631-638.

\* cited by examiner

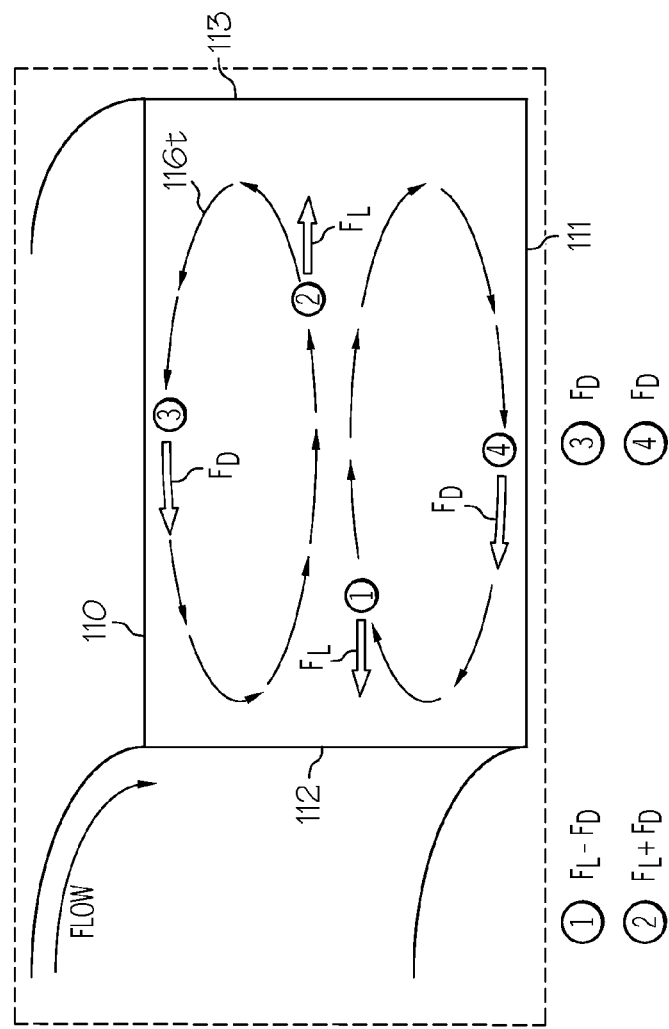
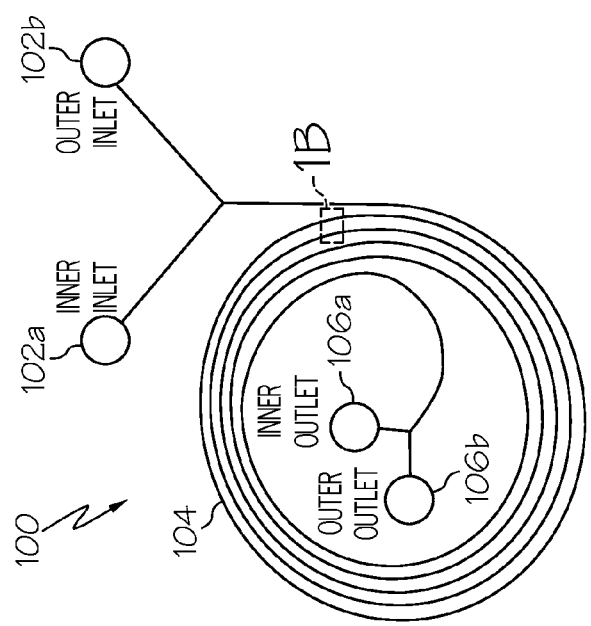
FIG. 1B
FIG. 1A

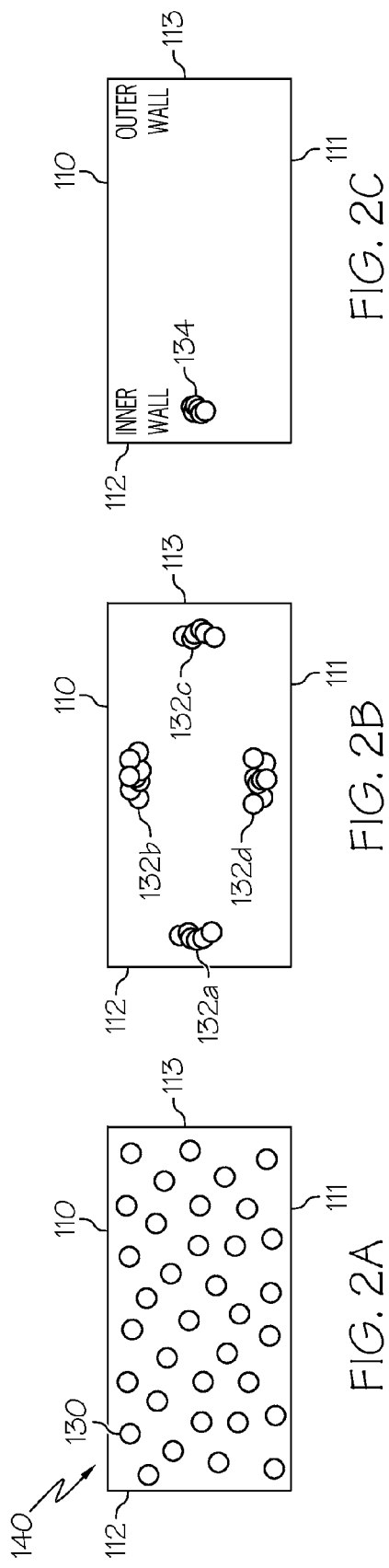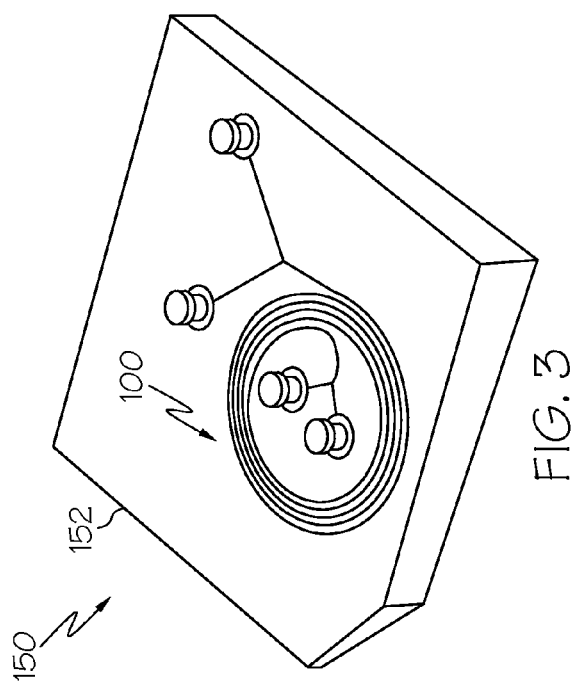

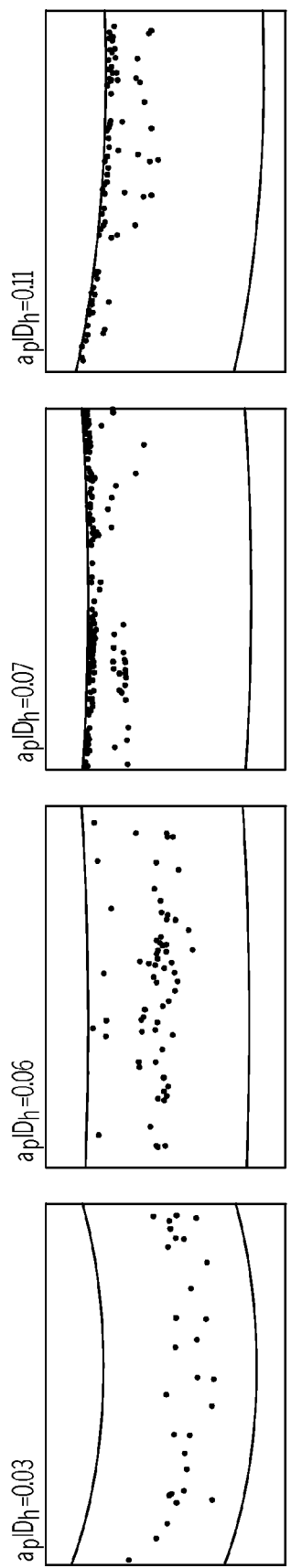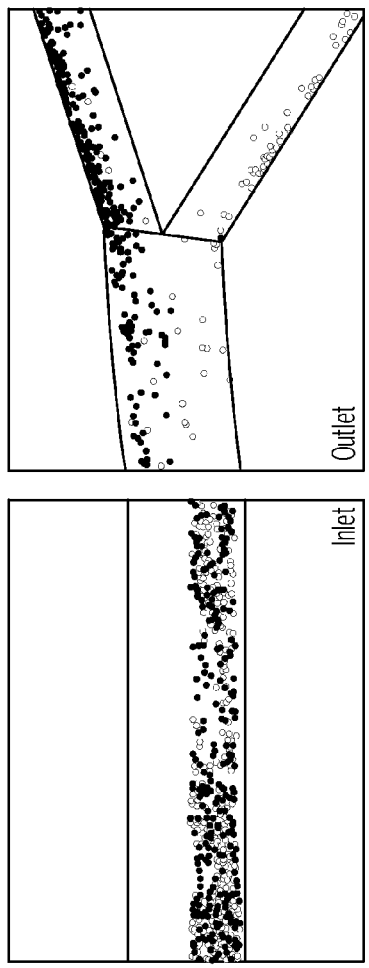
FIG. 6A  FIG. 6B  FIG. 6C  FIG. 6D
FIG. 7A  FIG. 7B

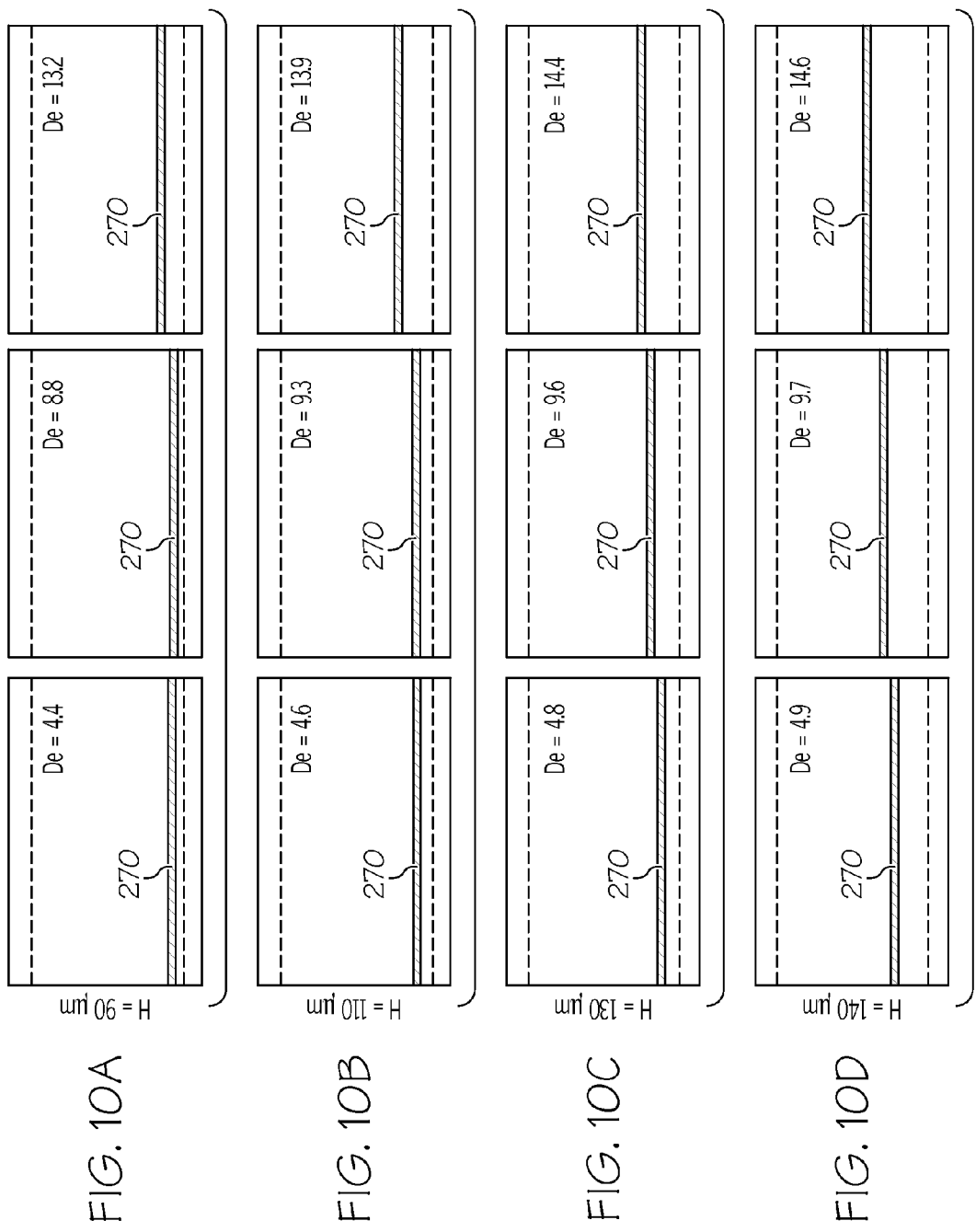

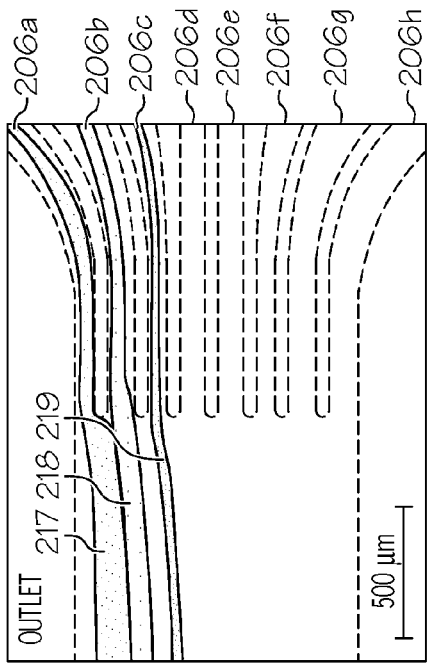
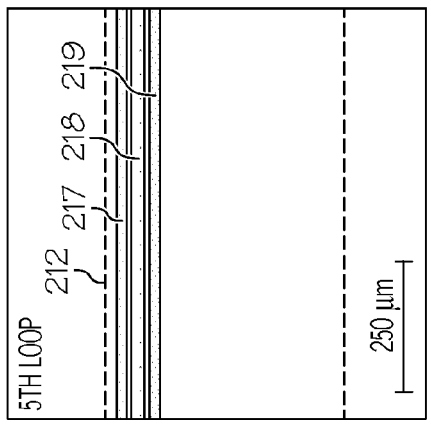
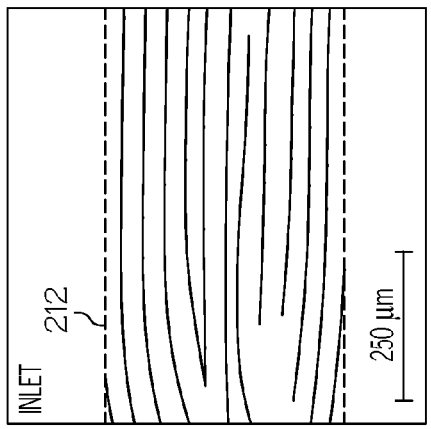
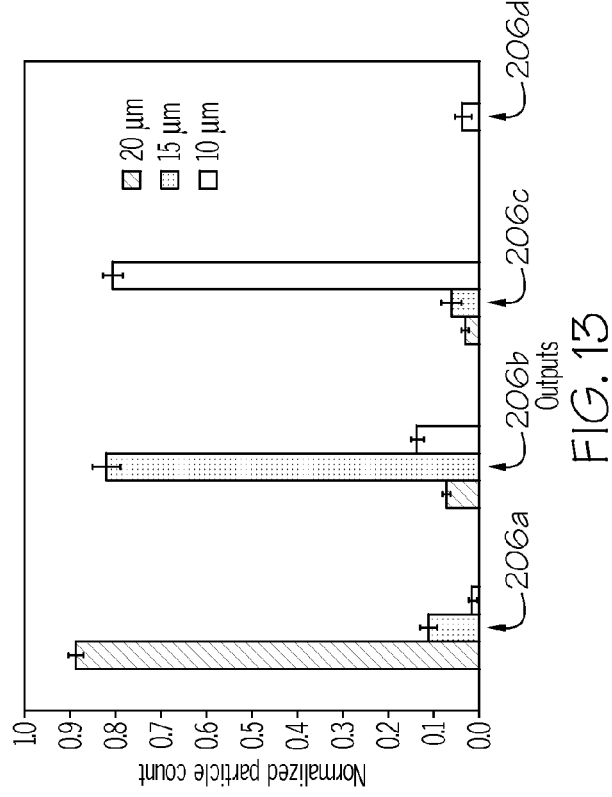
FIG. 12A
FIG. 12B
FIG. 12C
FIG. 13

SPIRAL MICROCHANNEL PARTICLE SEPARATORS, STRAIGHT MICROCHANNEL PARTICLE SEPARATORS, AND CONTINUOUS PARTICLE SEPARATOR AND DETECTOR SYSTEMS

CROSS-REFERENCE TO RELATED APPLICATIONS

The present application claims priority to U.S. Provisional Application No. 61/245,518, filed Sep. 24, 2009, entitled "Microfluidic Devices for Separation of Nanoparticles," which is hereby incorporated by reference in its entirety.

TECHNICAL FIELD

The present specification generally relates to the separation of particles within a homogeneous solution and, more particularly, to continuous spiral and straight microchannel particle separators as well as continuous particle separator and detection systems incorporating the same.

BACKGROUND

Separation and filtration of microparticles based on size may be important for many applications such as biochemical and environmental assays, micro/nano-manufacturing, and clinical analysis. Traditional methods for separation and removal of microparticles from solutions involve the use of a membrane filter, which are typically limited by the membrane pore size, making them inefficient for separating a wide range of particles. Clogging and high costs associated with membrane-based filtration on the microscale have resulted in the development of a number of membrane-less separation techniques. Sedimentation, field-flow fractionation (FFF), hydrodynamic chromatography (HDC), pinched flow fractionation (PFF), electrophoresis, dielectrophoresis, acoustic separation, diffusion-based extraction, deterministic lateral displacement, centrifugation, and inertial focusing are some of the techniques recently demonstrated for separation and concentration of particles and biological molecules.

However, microscale membrane-less separation techniques are not an attractive choice for filtering and separating particles in large sample volumes (~mL) due to long analysis times. In addition, the external force fields required for their functionality can potentially damage biological macromolecules and cells, and the active sources needed to produce these fields for particle manipulation often make the device fabrication complex and difficult to integrate with conventional LOC components. Finally, dependence on particle charge and mobility presents constraints on the type of particles that can be analyzed. Regarding passive membrane-less microfluidic devices, due to their small diffusion coefficients, large particles such as cells cannot be filtered efficiently as diffusion times and lengths become impractically long for most LOC applications.

Accordingly, alternative particle separator devices capable of continuous and complete separation of particles at low pressure drops and high throughputs are desired.

SUMMARY

In one embodiment, a spiral microchannel particle separator includes an inlet for receiving a solution containing particles, at least two outlets, and a microchannel arranged in a plurality of loops, the microchannel having a spiral radius of curvature R, a microchannel length L, and a hydraulic diameter $D_h$. Particles within a solution flowing through the spiral microchannel experience a lift force $F_L$ and a Dean drag force $F_D$. The spiral radius of curvature R and the hydraulic diameter $D_h$ of the spiral microchannel are such that for a flow rate U of the solution, the lift force $F_L$ and a Dean drag force $F_D$ are approximately equal and act in opposite directions for particles of a first size. The particles of the first size are focused in a single stream located at an equilibrium position near an inner wall of the microchannel, and the microchannel length L is such that the particles of the first size exit the spiral microchannel particle separator at a first outlet of the at least two outlets.

In another embodiment, a continuous particle separator and detection system includes a spiral microchannel particle separator, a rigid substrate layer, and a particle detector. The spiral microchannel particle separator includes an inlet for receiving a solution containing particles, at least two outlets, and a microchannel arranged in a plurality of loops, the microchannel having a spiral radius of curvature R, a microchannel length L, and a hydraulic diameter $D_h$. Particles within a solution flowing through the spiral microchannel experience a lift force $F_L$ and a Dean drag force $F_D$. The spiral radius of curvature R and the hydraulic diameter $D_h$ of the spiral microchannel are such that for a flow rate U of the solution, the lift force $F_L$ and a Dean drag force $F_D$ are approximately equal and act in opposite directions for particles of a first size. The particles of the first size are focused in a single stream located at an equilibrium position near an inner wall of the microchannel, and the microchannel length L is such that the particles of the first size exit the spiral microchannel particle separator at a first outlet of the at least two outlets. The spiral microchannel particle separator is bonded to the rigid substrate layer. The particle detector for detects particles of the first size focused in the single stream.

In yet another embodiment, a straight microchannel particle separator includes an inlet for receiving a solution containing particles, a central outlet, two side outlets, and a straight rectangular microchannel in fluid communication with the inlet, the central outlet, and the two side outlets. The straight rectangular microchannel includes two first walls of a first length and two second walls of a second length in cross-section. An aspect ratio of the first length to the second length is greater than 1.0 such that a shear rate of the solution flowing within the straight rectangular portion at a flow rate of $R_e > 50$ is modulated to focus particles of a first size along the two first walls of the straight rectangular portion by inertial migration. A length L of the straight rectangular microchannel is such that particles of the first size substantially migrate along the two first walls and exit the straight microchannel particle separator through the two side outlets and a remainder of the fluid, and particles that are not of the first size exit the straight microchannel particle separator through the central outlet.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 1A schematically depicts a spiral microchannel particle separator according to one or more embodiments described and illustrated herein;

FIG. 1B schematically depicts a cross-section of an inner loop of the spiral microchannel particle separator depicted in FIG. 1A according to one or more embodiments described and illustrated herein;

FIGS. 2A-2C schematically depict particle migration in the spiral microchannel particle separator depicted in FIG. 1A according to one or more embodiments described and illustrated herein;

FIG. 3 schematically depicts a spiral microchannel particle separator device including a rigid substrate layer according to one or more embodiments described and illustrated herein;

FIGS. 6A-6D schematically depict simulation results illustrating migration and equilibration of 1.9 µm, 4 µm, 5 µm, and 7.32 µm particles, respectively, across a microchannel outlet at De=0.47 according to one or more embodiments described and illustrated herein;

FIGS. 7A and 7B schematically depict complete separation of 1.9 µm and 7.32 µm particles at De=0.47 according to one or more embodiments described and illustrated herein;

FIG. 10A schematically depicts particle stream position variation of a spiral microchannel particle separator having a height of 90 µm at De=4.4, De=8.8, and De=13.2 according to one or more embodiments described and illustrated herein;

FIG. 10B schematically depicts particle stream position variation of a spiral microchannel particle separator having a height of 110 µm at De=4.6, De=9.3, and De=13.9 according to one or more embodiments described and illustrated herein;

FIG. 10C schematically depicts particle stream position variation of a spiral microchannel particle separator having a height of 130 µm at De=4.8, De=9.6, and De=14.4 according to one or more embodiments described and illustrated herein;

FIG. 10D schematically depicts particle stream position variation of a spiral microchannel particle separator having a height of 140 µm at De=4.9, De=9.7, and De=14.6 according to one or more embodiments described and illustrated herein;

FIGS. 12A-12C schematically depict particle migration at an inlet, fifth loop, and outlet, respectively, of a spiral microchannel particle separator according to one or more embodiments described and illustrated herein;

FIG. 13 graphically depicts particle counting results showing particle distribution across four outlets of the spiral microchannel particle separator illustrated in FIGS. 12A-12C according to one or more embodiments described and illustrated herein;

DETAILED DESCRIPTION

Figure 15:
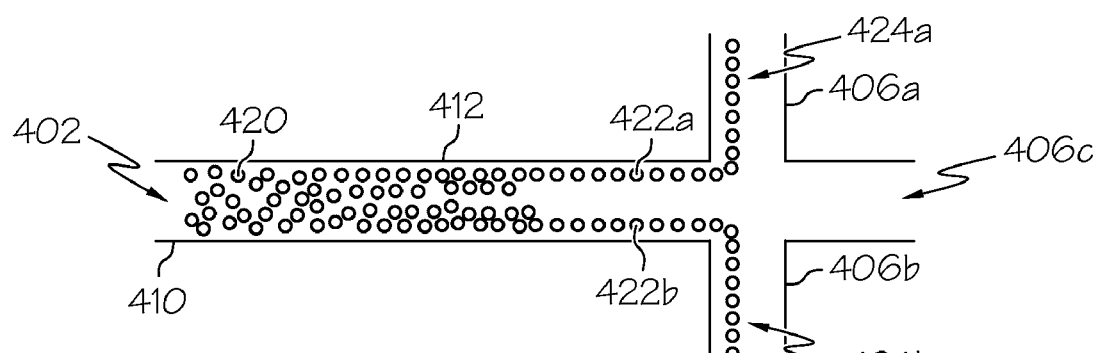
FIG. 15 schematically depicts a top view of a straight microchannel particle separator according to one or more embodiments described and illustrated herein.

FIG. 1A generally depicts one embodiment of a spiral microchannel particle separator for separating particles from a particle-laden solution. The design takes advantage of the inertial lift and viscous drag forces acting on particles of various sizes to achieve differential migration, and hence separation, of microparticles. The dominant inertial forces and the Dean rotation force due to the spiral microchannel geometry cause the larger particles to occupy a single equilibrium position near the inner microchannel wall. The smaller particles migrate to the outer half of the microchannel under the influence of Dean forces resulting in the formation of two distinct particle streams which may be collected in two separate outlets. FIG. 15 generally depicts a straight microchannel particle separator in which fluidic shear is modulated to result in preferential equilibration of particles along longer microchannel walls. Due to large lift forces generated by high aspect ratio channels, complete particle separation or filtration can be achieved in short distances even at low flow rates. Various embodiments of the spiral microchannel particle separators, straight microchannel particle separators, and continuous particle separator and detector systems are described in more detail herein.

Referring now to FIGS. 1A and 1B, one embodiment of a spiral microchannel particle separator 100 is schematically illustrated. The exemplary spiral microchannel particle separator 100 comprises an inner inlet 102a, an outer inlet 102b, a microchannel 104 arranged in a plurality of loops, an inner outlet 106a and an outer outlet 106b, all of which may be fabricated of a poly-dimethylsiloxane (PDMS) material. Alternatively, the above-components may be fabricated of polymethylmethacrolate (PMMA), polycarbonate (PC), or cyclic olefin copolymer (COC).

The inner inlet 102a and outer inlet 102b are configured to receive a particle-laden solution that contains particles of various sizes, and may be connected to ports or other coupling devices (e.g., configured to mate with a syringe) to allow the solution to enter the spiral microchannel particle separator 100. In an alternative embodiment, only one inlet may be provided, or in another embodiment, more than two inlets may be utilized.

The inner inlet 102a and outer inlet 102b are fluidly coupled to a spiral microchannel 104 that is arranged in a plurality of loops 104. FIG. 1B illustrates a cross-section view of the spiral microchannel 104. The microchannel 104 is rectangular in cross section, having two first walls 110, 111 and two second walls 112, 113. The first walls 110, 111 may be referred to herein as defining the width of the microchannel, while the second walls 112, 113 may be referred to herein as defining a height. However, no particular limitation is intended as to the orientation of the spiral microchannel particle separator 100.

The inner outlet 106a and outer outlet 106b are located at an opposite end of the spiral microchannel 104 from the inner inlet 102a and outer inlet 102b. As described in more detail herein, separated particles may be collected, detected, counted or otherwise analyzed at the inner and outer outlets 106a, 106b.

The design parameters of the spiral microchannel particle separator 100 may achieve a complete, or nearly complete, separation between two particle sizes using Dean drag to transpose smaller particles within the solution and inertial lift forces coupled with Dean drag to equilibrate larger particles within the solution. The combined effect of these forces results in the formation of distinct particle streams based on particle size, which in turn are collected at the inner outlet 106a and outer outlet 106b by taking advantage of the laminar flow in the spiral microchannel 104.

FIG. 1B illustrates forces acting upon particles flowing within the spiral microchannel 104. Fluid flowing through the spiral microchannel 104 experiences centrifugal acceleration directed radially outward leading to the formation of two counter-rotating vortices 116t, 116b known as Dean vortices in the top and bottom halves of the channel. The magnitude of these secondary flows is quantified by a dimensionless Dean number (De) given by:

$$De = \frac{\rho U_f D_h}{\mu} \sqrt{\frac{D_h}{2R}} = Re \sqrt{\frac{D_h}{2R}} \quad (1)$$

where ρ is the density of fluid medium (kg/m³), $U_f$ is the average fluid velocity (m/s), μ is the fluid viscosity (kg/m-s), R is the radius of curvature (m) of the path of the spiral microchannel 104, and Re is the flow Reynolds number. For a straight microchannel, De=0, indicating absence of Dean flows. In curved channels, De increases with higher curvature (smaller R), larger channel size (larger $D_h$), and faster flows (higher Re). Particles (labeled as particles 1-4 in FIG. 1B) flowing in a curvilinear channel experience a drag force due to the transverse Dean flows. Depending on particle size, this drag force ($F_D$) causes particles to move along the Dean vortices (i.e. circulate), and thus move towards either inner or outer channel wall.

In addition to the Dean drag $F_D$, particles in a curvilinear channel experience pressure forces and inertial lift forces. The net lift force ($F_L$) acting on the particles is a combination of the shear-induced inertial lift force $F_{IL}$ and the wall-induced inertial lift force $F_{WL}$. In Poiseuille flow, the parabolic nature of the velocity profile results in a fluidic shear-induced inertial lift force $F_{IL}$ that acts on particles and is directed away from the microchannel center. As the particles move towards microchannel walls, an asymmetric wake induced around particles generates a wall-induced inertial lift force $F_{WL}$ away from the wall. The magnitude of these opposing lift forces varies across microchannel cross-section, with the wall-induced lift forces dominating near the microchannel walls (e.g., inner wall 112 and outer wall 113) and the shear-induced lift forces dominating near the center of the microchannel 104. The particles thus tend to occupy equilibrium positions where the oppositely directed lift forces are equal and form narrow bands. It may be shown that preferential focusing of particles is dominant for particles with $a_p/D_h$ ratio ~0.1.

FIGS. 2A-2C schematically illustrate the principle of inertial migration. FIG. 2A illustrates particles 130 flowing within a straight microchannel 104'. FIG. 2B illustrates that for a rectangular microchannel 104, the number of equilibrium positions where the shear-induced lift force ($F_{IL}$) and the wall-induced lift forces ($F_{WL}$) balance each other reduces to four at low Re (positions 132a, 132b, 132c and 132d). As described in more detail below, adding a component of Dean drag ($F_D$) further reduces the four equilibrium positions to just one near the inner microchannel wall (position 134) illustrated in FIG. 2C.

Referring once again to FIG. 1B, particles dispersed in the spiral microchannel 104 get entrained in one of the two Dean vortices 116t, 116b that are formed at the top and bottom half of the microchannel 104. The Dean drag force and the inertial lift forces tend to dominate the migration of neutrally buoyant particles flowing in microchannels at Re~1. Particles (illustrated by particle 3 and particle 4) flowing near the top and bottom microchannel walls 110, 111 experience strong lateral flows due to Dean drag $F_D$ and are pushed towards the inner and outer microchannel walls 112, 113. Near the outer microchannel wall 113, the net lift force ($F_L$) acts along the direction of $F_D$ and the particles (particle 2) continue to follow the Dean vortices 116t, 116b independent of size. However, near the inner microchannel wall 112, $F_L$ and $F_D$ act in opposite directions and depending on the magnitude of these forces, particles (particle 1) will either equilibrate and form a focused stream or continue to re-circulate in the Dean vortex.

As described below, the size dependence of the forces that act on particles flowing in spiral microchannel, namely the Dean drag and the inertial lift forces, are manipulated to produce a focused stream of particles of a similar size. The particles may be referred to as first particles of a first size. All other particles not of the first size continue to circulate within the Dean vortices. As an example and not a limitation, a solution may contain first particles having a diameter of 7.32 μm ($a_p/D_h$~0.1) and smaller second particles having a diameter of 1.9 μm ($a_p/D_h$~0.03). It should be understood that embodiments are not limited to these diameters, and that these diameters were chosen for illustrative purposes.

The spiral geometry of the spiral microchannel particle separator 100 causes the bigger 7.32 μm particles to occupy a single equilibrium position near the inner microchannel wall 112. On the other hand, the smaller 1.9 μm particles experience higher viscous drag due to the Dean flows and will continue to re-circulate along the Dean vortices 116t, 116b and can be transposed to the outer half of the microchannel 104. Thus, the spiral microchannel particle separator 100 uses inertial migration of larger particles and the influence of Dean drag on smaller particles to achieve a complete separation of 1.9 μm and 7.32 μm polystyrene particles.

To illustrate the concepts of using inertial migration and Dean drag to separate particles within a spiral microchannel, a spiral microchannel particle separator device 150 was fabricated as illustrated in FIG. 3. A spiral microchannel particle separator 100 was fabricated in polydimethylsiloxane (PDMS, Sylgard 184, Dow Corning). The design comprised of a 5-loop spiral geometry with two inlets and two bifurcating outlets. The microchannels were 100 μm wide and 50 μm high with 250 μm spacing between two successive loops. The initial radius of curvature R of the spiral was 3 mm and the total length L of the microchannel was ~13 cm.

The spiral microchannel was fabricated using standard soft lithography methods. A 50 μm thick layer of SU-8 photoresist (2075, Microchem Corp.) was patterned on a single-side polished 3" silicon wafer using conventional photolithography techniques. PDMS prepolymer mixed in a 10:1 ratio with the curing agent was then cast on the SU-8 master to replicate microchannel features. After curing, the PDMS mold was peeled from the SU-8 master and $O_2$ plasma bonded to a 1 mm thick glass substrate layer 152 to complete the spiral microchannel particle separator device 150. Input and output ports were cored using a 14 gauge syringe needle prior to bonding.

To experimentally evaluate particle separation, one syringe was filled with fluorescently labeled polystyrene particles (Bangs Laboratories) in DI water (0.05% volume fraction) while the other with DI water only. Using syringe pumps (NE-1000X, New Era Pump Systems) two 5 cc syringes were driven at 5 μL/min ($U_f$=33 mm/s, De=0.23), 10 μL/min ($U_f$=66 mm/s, De=0.47) and 20 μL/min ($U_f$=130 mm/s, De=0.94).

Presence of Dean flows and their extent in spiral microchannel particle separator device 150 was confirmed numerically by modeling dye flows at various flow conditions. At lower Dean number (De=0.23), the dye gradually moves from the outer inlet 106b towards the inner outlet 106a following the Dean vortices. The magnitude of these Dean vortices increases with increasing fluid velocity due to the higher centrifugal force acting on the fluid. At De=0.47, the two dyes have switched positions by the time the flow reaches the outlets. Further increasing the flow rate to De=0.94 results in a complete recirculation of the two dyes by the time the flow reaches the outlet. These results suggest that for microchannel geometry, De~1 is high and results in complete flow recirculation. Because embodiments described herein are focused on particle separation, complete recirculation is counter-productive and should be avoided. Therefore, flows should be limited to De<1, which corresponds to maximum input flow of 20 μL/min or Re~10.

The average Dean velocity for a given De may be expressed as:

$$\overline{U}_{Dean}=1.8\times10^{-4}De^{1.63} \text{ (m/s)} \qquad (2)$$

Depending on particle size, these transverse secondary Dean flows tend to entrain particles in one of the two vortices formed and force them to follow fluid movement within the vortices. The drag force exerted on particle due to these flows can then be obtained by assuming the Stokes drag:

$$F_D=3\pi\mu\overline{U}_{Dean}a_p=5.4\times10^{-4}\pi\mu De^{1.63}a_p(N) \qquad (3)$$

In addition to the Dean drag, the neutrally buoyant particles also experience shear induced inertial lift forces and wall induced lift forces. The viscous drag force is responsible for the particles flowing in the channel and has no consequence in differential migration of particles. To account for the lift forces (the inertial and wall-induced), an expression describing the magnitude of the lift forces as a function of the particle position across the channel cross-section. may be:

$$F_L=pG^2C_La_p^4(N) \qquad (4)$$

where G is the shear rate of the fluid (1/s) and $C_L$ is the lift co-efficient which is a function of the particle position across the channel cross-section assuming an average value of 0.5. The average value of G for a Poiseuille flow is given by G=$U_{max}/D_h$, where, $U_{max}$ is the maximum fluid velocity (m/s) and can be approximated as $2 \times U_f$. From these expressions, the two forces ($F_D$ and $F_L$) depend on the particle size ($a_p$), with the lift force ($F_L$) increasing rapidly for increasing particle size ($F_L \propto a_p^4$ while $F_D \propto a_p$). By varying the ratio of these two forces, differential migration of particles based on size may be used to achieve a separation of a mixture of 1.9 μm and 7.32 μm polystyrene particles.

Experimental Dean drag forces ($F_D$) and the net lift forces ($F_L$) acting on 1.9 μm and 7.32 μm particles flowing in a 100×50 μm (W×H) microchannel at the three Dean numbers tested using the above-described device 150 are summarized in Table 1.

TABLE 1

| Particle size (μm) | Dean number (De) | $F_D$ (N) | $F_L$ (N) |
|---|---|---|---|
| 1.9 | 0.23 | $3 \times 10^{-13}$ | $6.5 \times 10^{-15}$ |
|  | 0.47 | $9 \times 10^{-13}$ | $2.6 \times 10^{-14}$ |
|  | 0.94 | $3 \times 10^{-12}$ | $1 \times 10^{-13}$ |
| 7.32 | 0.23 | $1.1 \times 10^{-12}$ | $1.4 \times 10^{-12}$ |
|  | 0.47 | $3.6 \times 10^{-12}$ | $5.7 \times 10^{-12}$ |
|  | 0.94 | $1.1 \times 10^{-11}$ | $2.3 \times 10^{-11}$ |

The Dean forces dominate over the lift forces and influence the migration of 1.9 μm particles for all three flows. The 1.9 μm particles are then expected to get entrained in the Dean vortices and re-circulate along with the fluid flow. For 7.32 μm particles, the Dean drag forces acting on the particles at the three flows are less than the corresponding net lift forces. Thus, for 7.32 μm particles the lift forces dominate and the particles remain unperturbed by the Dean vortices and continue to flow in the same manner as in a straight microchannel.

Experimental data and schematic depictions that illustrate distribution of 1.9 μm particles across the microchannel are shown in FIGS. 4A-I. With general reference to FIGS. 4A-4I, at De=0.23, the 1.9 μm particles were uniformly distributed across the width of the channel at the outlet due to the weak Dean forces that are not sufficient to move all particles towards the outer half of the microchannel. When the flow was increased to De=0.47, the particles experience greater $F_D$, and nearly 95% of the particles migrated from the inner half at the inlet to the outer half by the time the flow reached the outlet. Increasing flow further to De=0.94 resulted in a complete transfer of particles to the outer half in the second loop due to stronger Dean flows, and a complete re-circulation by the time the particles reach the outlet.

Figure 4C:
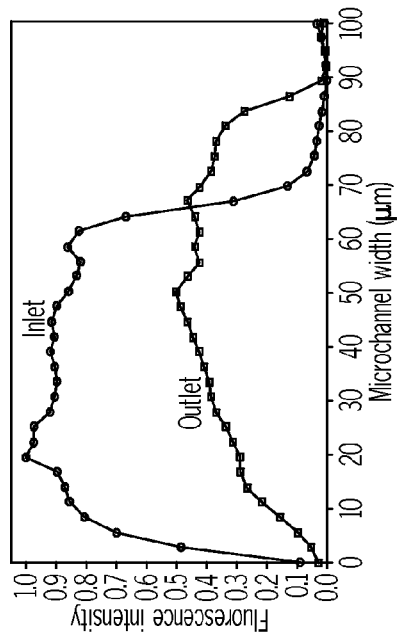
FIGS. 4C, 4F, and 4I graphically depict normalized particle dispersion across a microchannel width De=0.23, De=0.47, and De=9.4, respectively, according to one or more embodiments described and illustrated herein.
Figure 4F:
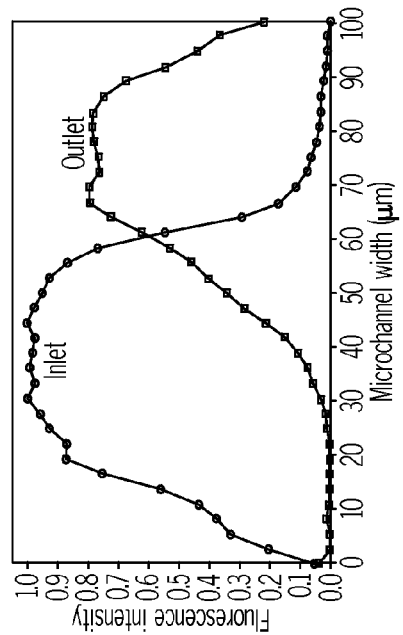
Figure 4B:
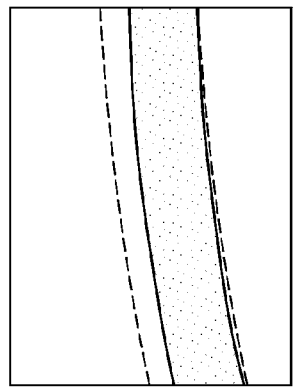
FIGS. 4B, 4E, and 4H schematically depict 1.9 µm particles migration across a microchannel outlet for De=0.23, De=0.47, and De=9.4, respectively, according to one or more embodiments described and illustrated herein.
Figure 4E:
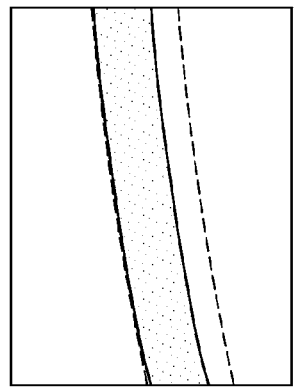
Figure 4A:
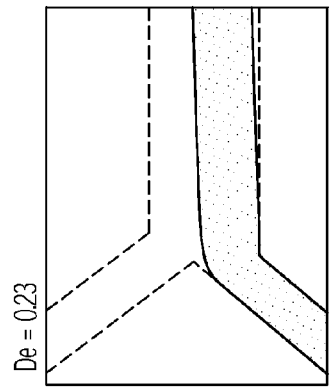
FIGS. 4A, 4D, and 4G schematically depict 1.9 µm particles across a microchannel inlet for De=0.23, De=0.47, and De=9.4, respectively, according to one or more embodiments described and illustrated herein.
Figure 4D:
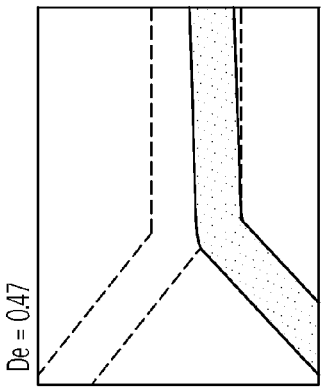
Figure 4I:
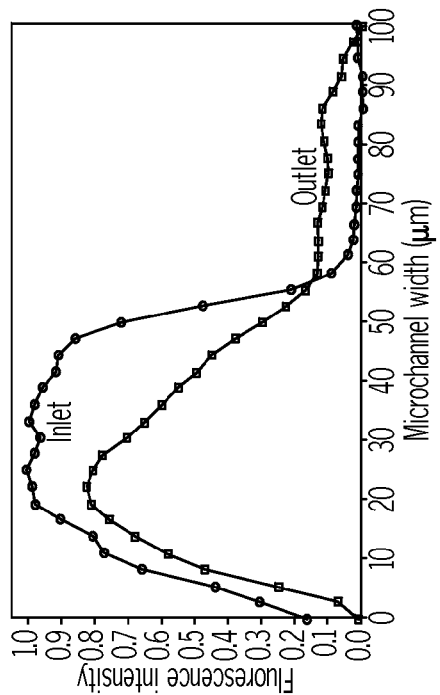
Figure 4H:
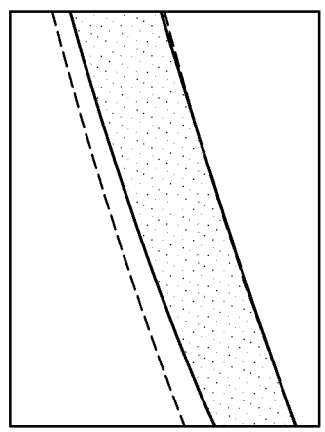
Figure 4G:
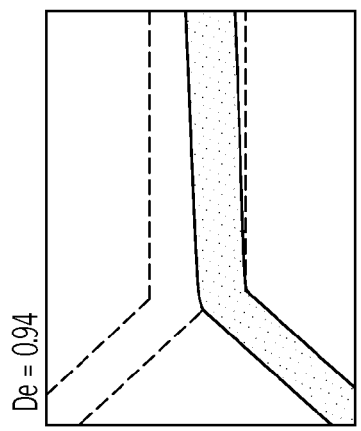
Figure 5A:
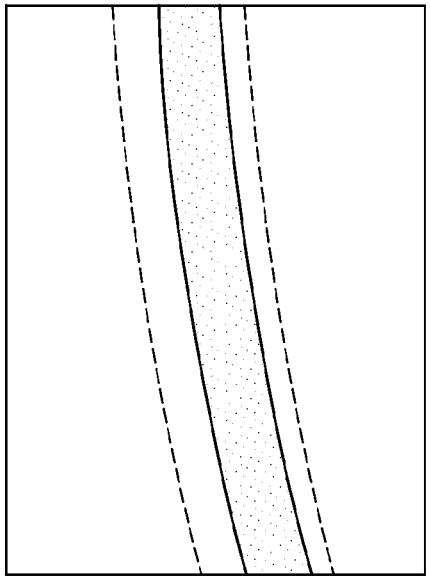
FIG. 5A schematically depicts 7.32 µm particles introduced at an inner microchannel inlet for De=0.47 according to one or more embodiments described and illustrated herein.
Figure 5B:
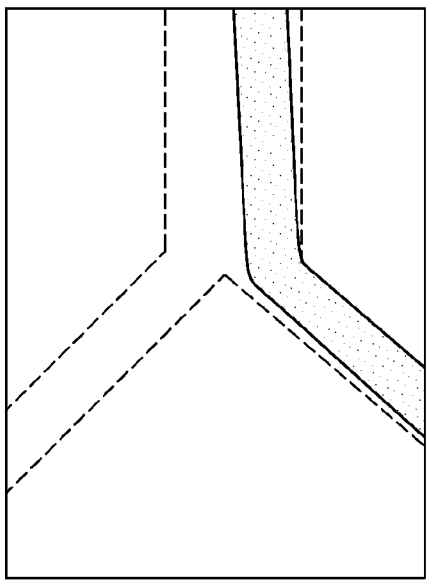
FIG. 5B schematically depicts a microchannel outlet and the flow of the 7.32 µm particles introduced at the inner microchannel inlet for De=0.47 illustrated in FIG. 5A according to one or more embodiments described and illustrated herein.
Figure 5C:
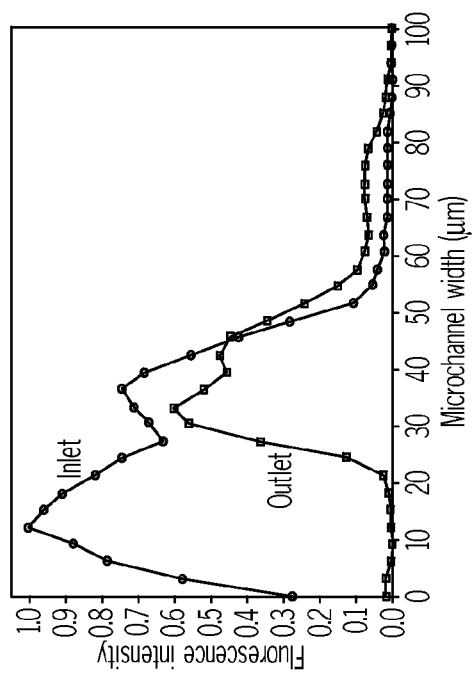
FIG. 5C graphically depicts normalized distribution of 7.32 µm particles illustrated in FIG. 5B according to one or more embodiments described and illustrated herein.
Figure 5D:
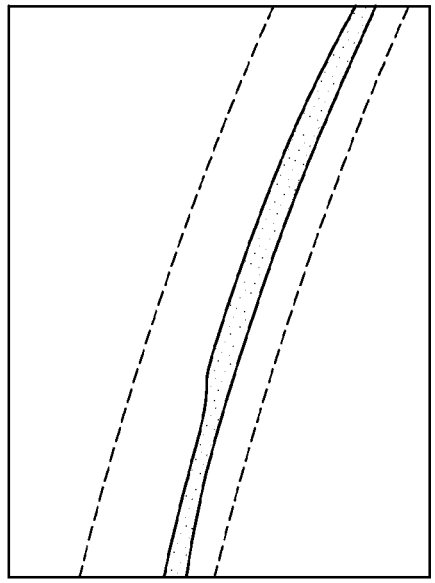
FIG. 5D schematically depicts 7.32 µm particles introduced at an outer microchannel inlet for De=0.47 according to one or more embodiments described and illustrated herein.
Figure 5E:
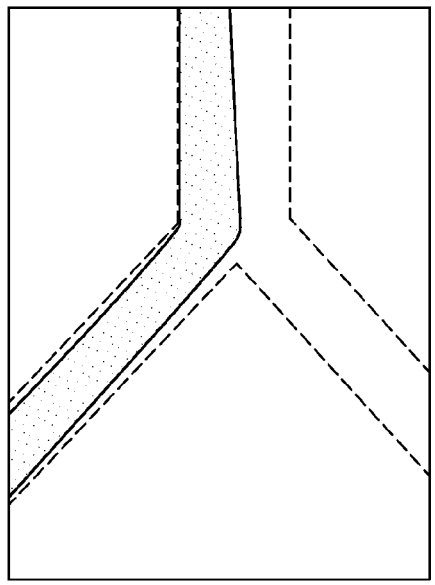
FIG. 5E schematically depicts a microchannel outlet and the flow of the 7.32 µm particles introduced at the outer microchannel inlet for De=0.47 illustrated in FIG. 5D according to one or more embodiments described and illustrated herein.
Figure 5F:
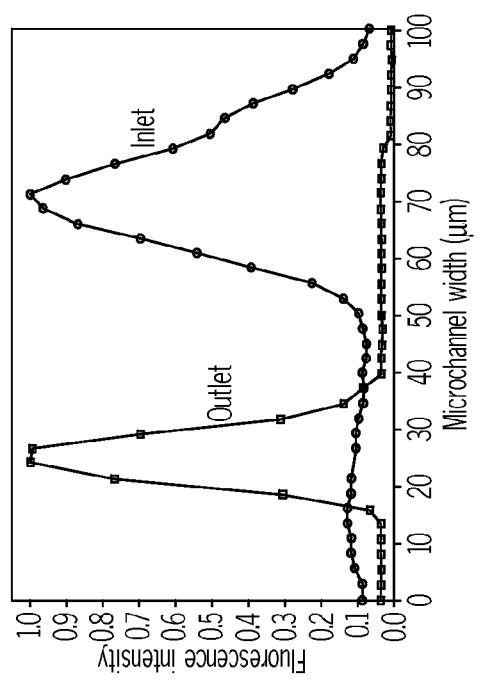
FIG. 5F graphically depicts normalized distribution of 7.32 µm particles illustrated in FIG. 5E according to one or more embodiments described and illustrated herein.

To verify the inertial migration and equilibration near the inner microchannel wall 212, the larger 7.32 μm particles were introduced into the spiral geometry through the inner and outer outlet. FIGS. 5A-5F illustrate the averaged experimental images confirming particle distribution across the microchannel 104 for 7.32 μm particles introduced through the inner and outer inlet at De=0.47. Also illustrated are the normalized distribution of 7.32 μm particles at the microchannel inlet and outlet. Irrespective of where the particles were introduced into the microchannel (i.e., the inner or outer inlet), at the outlet the particles tend to form a narrow band of particles focused towards the inner wall for all three flow velocities, unlike the 1.9 μm particles. This behavior is primarily attributed to the inertial migration and equilibration of the particles due to stronger lift forces. For 100×50 μm microchannel dimensions, the hydraulic diameter is $D_h$=67 μm and thus for 7.32 μm particles $a_p/D_h$=0.11 (>0.1), which yields particle equilibration. The lift forces then align the particles in the four equilibrium positions as was schematically depicted in FIG. 1B. Due to the curvilinear nature of the spiral geometry of the spiral microchannel particle separator 100 and strong lateral Dean flows at the top and bottom of the microchannel 104, the equilibrium positions were further reduced to one near the inner wall 212, as FIGS. 5A-5B illustrate.

Inertial migration and equilibration of particles is highly size dependent. To illustrate the threshold $a_p/D_h$ ratio above which particles begin focusing in the spiral microchannel particle separator 100, polystyrene particles 1.9 μm, 4 μm, 5 μm, and 7.32 μm in diameter were modeled. FIGS. 6A-6D show simulated particle migration across the microchannel outlet 106a, 106b at De=0.47; all particles were introduced through the inner inlet 102a of the microchannel 104 (see FIG. 1A). The results show that the 1.9 μm particles ($a_p/D_h$=0.03) and the 4 μm particles ($a_p/D_h$=0.06) are more influenced by the Dean forces rather than the inertial lift force, and thus follow the fluid flow migrating away from the inner wall of the microchannel. However, the 5 μm ($a_p/D_h$=0.07) and the 7.32 μm ($a_p/D_h$=0.11) particles migrate and equilibrate near the inner microchannel wall. Therefore, particles with $a_p/D_h \geq 0.07$ tend to focus and occupy a single equilibrium position. This suggests that a complete separation between particles smaller and larger than the 5 μm threshold is possible.

The determination of a length L of the spiral microchannel 104 to achieve a complete separation between 1.9 μm and 7.32 μm particles will now be described. The length L should be long enough to enable the 1.9 μm particles to migrate to the outer half of the microchannel 104 and for the 7.32 μm particles to focus near the inner wall 112 (see FIGS. 1A and 1B). Particles of the two sizes may then be collected separately at the two outlets 106a, 106b. Using Asomolov's lift force equation and assuming Stokes drag, expression for the particle lateral migration velocity ($U_L$) can be written as:

$$U_L = \frac{\rho U_{max}^2 a_p^3 C_L}{3\pi \mu D_h^2} \text{ (m/s)} \quad (5)$$

The channel length ($L_I$) for the particle to completely focus at one of the equilibrium positions is then given by:

$$L_I = \frac{U_f}{U_L} \times L_M \text{ (m)} \quad (6)$$

where $L_M$ is the migration length (m). Similarly, the channel length required for Dean migration ($L_D$) may be given by:

$$L_D = \frac{U_f}{U_{Dean}} \times L_M \text{ (m)} \quad (7)$$

For 1.9 μm particles to migrate over a distance of 100 μm (or ~2×channel half width) to ensure that all particles from the inner half of the microchannel 104 migrate into the outer half of the microchannel 104, the appropriate channel lengths are calculated to be 20 cm, 12.5 cm and 8 cm for De=0.23, De=0.47 and De=0.94 flows, respectively. Thus, De=0.47 flow is appropriate for the 13 cm long microchannel in this work. For 7.32 μm particles at De=0.47 to migrate over a length scale of 50 μm to ensure that all particles occupy equilibrium positions, 16 cm of microchannel length L may be needed. However, as Dean flows in the spiral microchannel particle separator 100 may actually aid lateral migration of particles toward their equilibrium positions, it may be expected that the microchannel length L for particle focusing to be less than the value calculated from Eq. 6. Therefore, a 13 cm long spiral microchannel 104 of with at De=0.47 should yield a complete separation of the 1.9 μm and 7.32 μm particle mixture.

To experimentally demonstrate particle separations, a mixture of 1.9 μm and 7.32 μm particles (0.05% volume fraction) was introduced through the inner inlet 102a of the spiral microchannel particle separator device 150 illustrated in FIG.

Figure 7C:
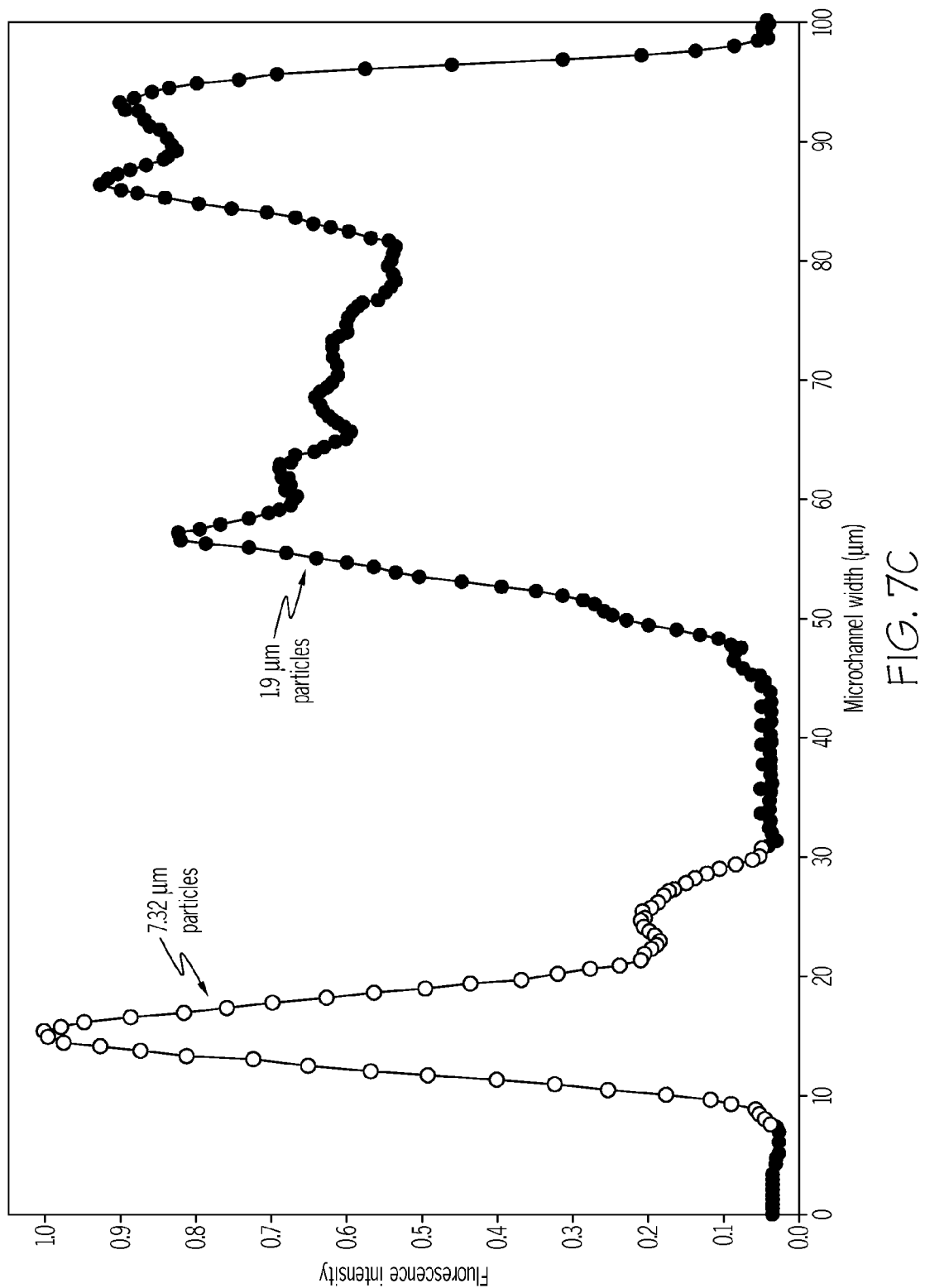
FIG. 7C graphically depicts normalized distribution of 1.9 µm and 7.32 µm for De=0.47 according to one or more embodiments described and illustrated herein.

3. It should be understood that the present example is illustrative and not limiting purposes. For visualization, the two particle types were labeled using with different fluorophores: the 1.9 μm were labeled with Plum Purple and 7.32 μm with Dragon Green. Images at the inlet and outlet of the spiral microchannel were captured using DAPI and FITC filter cubes. FIG. 7A is a schematic illustration of the overlaid images at the inlet, and FIG. 7B is a schematic illustration of the overlaid images at the two outlet positions. Although the particle mixture was introduced through the inner inlet, by the time the flow reached the outlet, the 1.9 μm particles have all migrated into the outer half of the channel and were collected at the outer outlet. On the other hand, the 7.32 μm particles occupied the equilibrium position near the inner microchannel wall and were collected at inner outlet. A line scan through the microchannel output (immediately prior to bifurcation) indicating the normalized particle dispersion across the microchannel is shown in FIG. 7C. Accordingly, the particles of the two sizes were successfully separated from one another using the spiral geometry described above.

It is noted that in non-particle separating applications, such as cytometry, embodiments may comprise of a single inlet and a single outlet to focus particles of a particular size in a single stream. In this manner, a sheath-less high-throughput flow cytometry system may be realized without requiring complex plumbing controls associated with sheath-based cytometer systems. Particles may be focused into a single stream by inertial forces and Dean drag as described above for counting and detecting purposes.

Figure 8B:
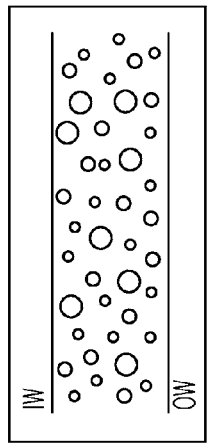
FIGS. 8A-8D schematically depict a spiral microchannel particle separator having eight outlets according to one or more embodiments described and illustrated herein.
Figure 8C:
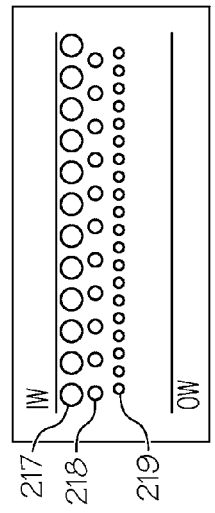
Figure 8D:
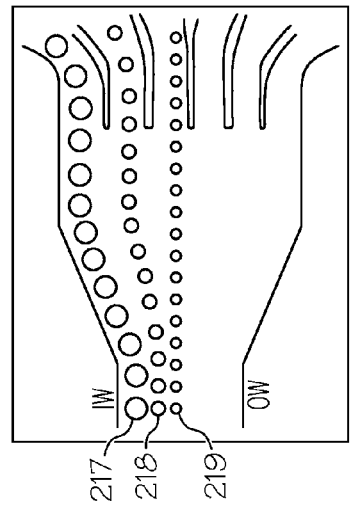
Figure 8A:
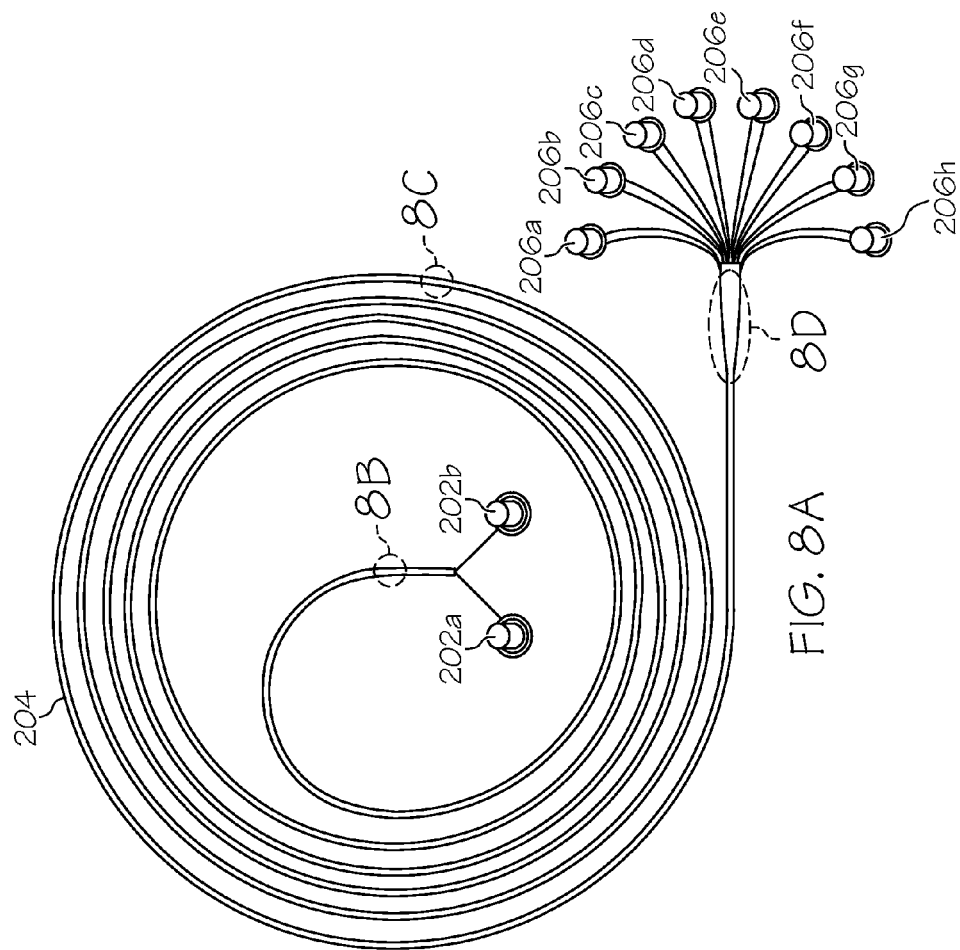

Referring now to FIGS. 8A-8D, another embodiment of the spiral microchannel particle separator 200 is illustrated. The exemplary spiral microchannel particle separator 200 comprises an inner inlet 202a, an outer inlet 202b, and eight outlets 206a-h as illustrated in FIG. 8A. It should be understood that in some embodiments, only one inlet may be utilized. Alternatively, more than two inlets may be used. Further, more or fewer outlets may be present. The spiral microchannel particle separator 200 has a spiral microchannel 204 that is arranged in a plurality of loops. In the illustrated embodiment, five loops are present from the inlets 202a, 202b to plurality of outlets 206a-h.

A combination of Dean drag and inertial lift forces result in particle equilibration at the inner microchannel wall 212. The position at which the particles equilibrate is dependent on the ratio of these two forces. The geometric properties of the spiral microchannel particle separator 200 exploits the particle size dependence of the ratio of the two forces to form segregated, focused particles streams (illustrated by particle streams of particle sizes A, B and C of FIG. 9) that can be extracted by the outlets 206a-h. As illustrated in FIG. 8B, a particle-laden solution comprising particle sizes A, B and C are introduced at the inner and/or outer inlets 202a, 202b. The particles of each size are co-mingled within the microchannel 204. Within the spiral microchannel 204, the particles begin to be focused into streams by particle size. As shown in FIG. 8C, particles of size A, which are the largest particles, are focused into a first stream 217 closest to the inner wall 212. Particles of size B, which is smaller than size A, are focused in a second stream 218 next to the stream of size A particles. Particles of size C, which is smaller than size B, are focused in an outer-most third stream 219.

A wide segment 207 may be located prior to the plurality of outlets 206a-h to aid in directing the streams of particles 217, 218, and 219 to the designated outlet. Separation between the individual particle streams is enhanced by the opening of the spiral microchannel 204 into the wide segment 207 before extracting the individual streams at the plurality of outlets 206a-h. Referring to FIG. 8D, the plurality of outlets 206a-h are arrange to receive the focused streams of particles. First particle stream 217 comprising the larger particles of size A exits the spiral microchannel particle separator 200 at outlet 206a, second particle stream 218 comprising the particles of size B exits the spiral microchannel particle separator 200 at outlet 206b, and the smallest particles of size C exits the spiral microchannel particle separator 200 at outlet 206c.

Figure 9:
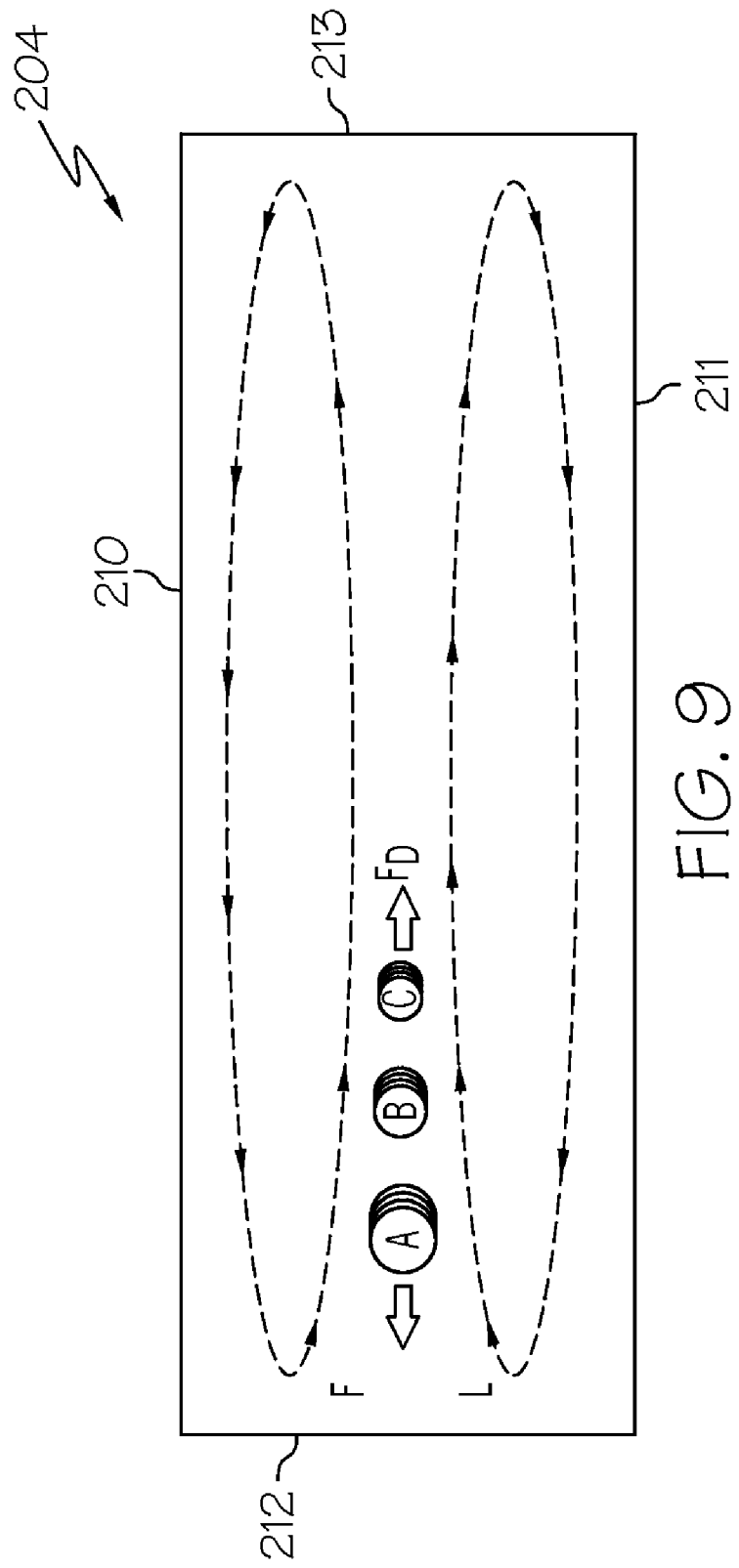
FIG. 9 schematically depicts a cross-section of an inner loop of the spiral microchannel particle separator depicted in FIGS. 8A-8D according to one or more embodiments described and illustrated herein.

As described above, particle equilibration in rectangular microchannel cross-sections is independent of $P_h$, and rather depends on the shortest channel dimension (microchannel height, H) due to varying shear rates across the channel cross-section. Hence, the criterion for particle focusing is $a_p/H \geq 0.07$. This result may be used to design low aspect ratio spiral microchannels to enhance the separation between individual particle streams over a wide range of particle sizes. The dependence of ratio of the lift force ($F_L$) to Dean drag force ($F_D$) on particle size ($F_L/F_D \alpha a_p^3$) and the shear rate modulation in low aspect ratio microchannels may be exploited to separate particles of three different sizes. FIG. 9 illustrates a microchannel 204 cross section and the effects of $F_L$ and $F_D$ on particles. The ratio of forces ($F_L/F_D$) is the determining factor in where a particle of a given size (diameter) equilibrates (e.g., within streams or particles sizes A, B, or C). The dominant inertial lift forces align the randomly distributed particles at the inlet near the inner microchannel wall as the flow progresses downstream. On the other hand, the significant Dean drag force move these focused streams farther away from the channel wall depending on the particle size, with the largest particle being closest to the inner channel wall. This results in the evolution of three distinct particle streams which can be independently extracted by designing appropriate outlets.

To illustrate the concepts of using inertial migration and Dean drag to separate particles within a spiral microchannel into multiple particle streams, a spiral microchannel particle separator devices were fabricated as illustrated in FIG. 8A. The fabricated devices consisted of a five loop Archimedean spiral microchannel with two inlets and eight equally spaced outlets. The spiral designs had an initial radius of curvature of 1 cm, with spacing between the successive spiral loops fixed at 500 μm. The width of the microchannel devices was fixed at 500 μm, while microchannel height was varied from 90 μm to 140 μm. At the outlet, the 500 μm wide channel opened into a 1 mm wide segment to increase spacing between particle streams before splitting into eight 100 μm wide outlets. The microchannel devices were fabricated in polydimethylsiloxane (PDMS, Sylgard 184, Dow Corning) using standard soft lithography methods as described above.

Fluorescently labeled polystyrene particles were diluted in DI water before testing (~0.05% volume fraction). A syringe pump (KDS101, KDScientific Inc.) was used to drive syringes filled with the particle solution. To evaluate particle stream positions within the microchannel, high speed images of the microchannel were captured using an inverted epi-fluorescence microscope (IX71, Olympus Inc.) equipped with a 12-bit CCD camera (Retiga EXi, QImaging). Using ImageJ® software, Z-stacked composite images were generated by overlaying a stack of 300 images. The particle stream position was determined by analyzing the grayscale line scans across the channel width in the composite image.

To demonstrate separation of particle mixtures, a solution containing 10 μm (σ=0.54 μm), 15 μm (σ=0.98 μm), and 20 μm (σ=0.5 μm) diameter polystyrene particles labeled with DAPI, FITC, and TRITC fluorophores respectively was used. The particle streams were viewed and captured separately using appropriate filter cubes. The individual images were super-imposed to create a composite image to display the formation of three separate focused particle streams.

To quantify separation efficiency, the outlet streams at each of the eight outlets were collected in separate vials and a flow cytometry analysis was performed. The LSR BD II flow cytometer was used to perform the analysis. Individual particles solutions were used as controls to draw the gates on a FSC vs. SSC plot. The collected samples were then run to determine the particle count for each of the three particles in all the eight outlets.

To demonstrate cell separations, SH-SY5Y neuroblastoma cells ~15 μm (σ=5 μm) in diameter were cultured in Opti-MEM medium containing 10% fetal bovine serum supplemented with L-glutamine. The C6 rat glioma cells ~8 μm (σ=3 μm) in diameter were cultured in Ham's F-12 medium containing 15% horse serum and 5% fetal bovine serum supplemented with 0.25 μg/mL amphotericin B, 100 U/mL penicillin, and 100 μg/mL streptomycin. Prior to testing, the cells were mixed together and diluted in 1× phosphate buffered saline (PBS) solution (0.05% volume fraction). The SH-SY5Y neuroblastoma cells were labeled with Cell-Tracker™ Green (Invitrogen Corp.) for better visualization and to confirm separation.

As described above, embodiments described herein take advantage of the particle size dependence of the ratio of $F_L$ and $F_D$ in spiral microchannels to separate 10 μm, 15 μm and 20 μm diameter particles. Before testing the particle mixture, particles were tested individually in channels of varying heights and De. For each channel height, De was increased by increasing the flow rate until a single focused particle stream formed at the outlet. Increasing the flow rate further, resulted in migration of the focused particle stream away from the channel inner wall towards the channel center. As the flow rate increased further, the Dean forces began to dominate the inertial lift forces, resulting in de-focusing of the particle stream. The equilibrium positions of the particle streams were recorded as a function of De, and these results were used to select the optimum channel height and flow rate required to demonstrate multi-particle separation.

FIGS. 10A-10D schematically illustrate composite images indicating the position (x) of the 10 μm diameter particle streams as a function of De in microchannels of varying height (H=90 μm 140 μm). The suspension of 10 μm diameter particles was introduced through both inlets and all images were captured in the 500 μm section just prior to the outlet. For a given channel height, the focused particle stream 270 moved away from the inner microchannel wall 212 at increasing De, indicating the dominance of the Dean force. Although an increase in flow velocity resulted in a greater lift force ($F_L \propto U_f^2$) as compared to the Dean drag ($F_D \propto U_f^{1.63}$), the stream movement away from the wall may be explained by the decrease in the lift co-efficient with increasing fluid flow velocity. Hence, the net lift force reduces with increasing flow velocity, and the particle stream 270 moves away from the inner microchannel wall. Increasing the channel height also resulted in focusing of particle streams further away from the inner microchannel wall, which may be explained by the fact that for a given flow velocity $U_f$ the Dean drag force increases with channel height, while the lift force decreases with increasing channel height. Thus, the particle stream position may be altered by either increasing the De or increasing the channel height.

Figure 11A:
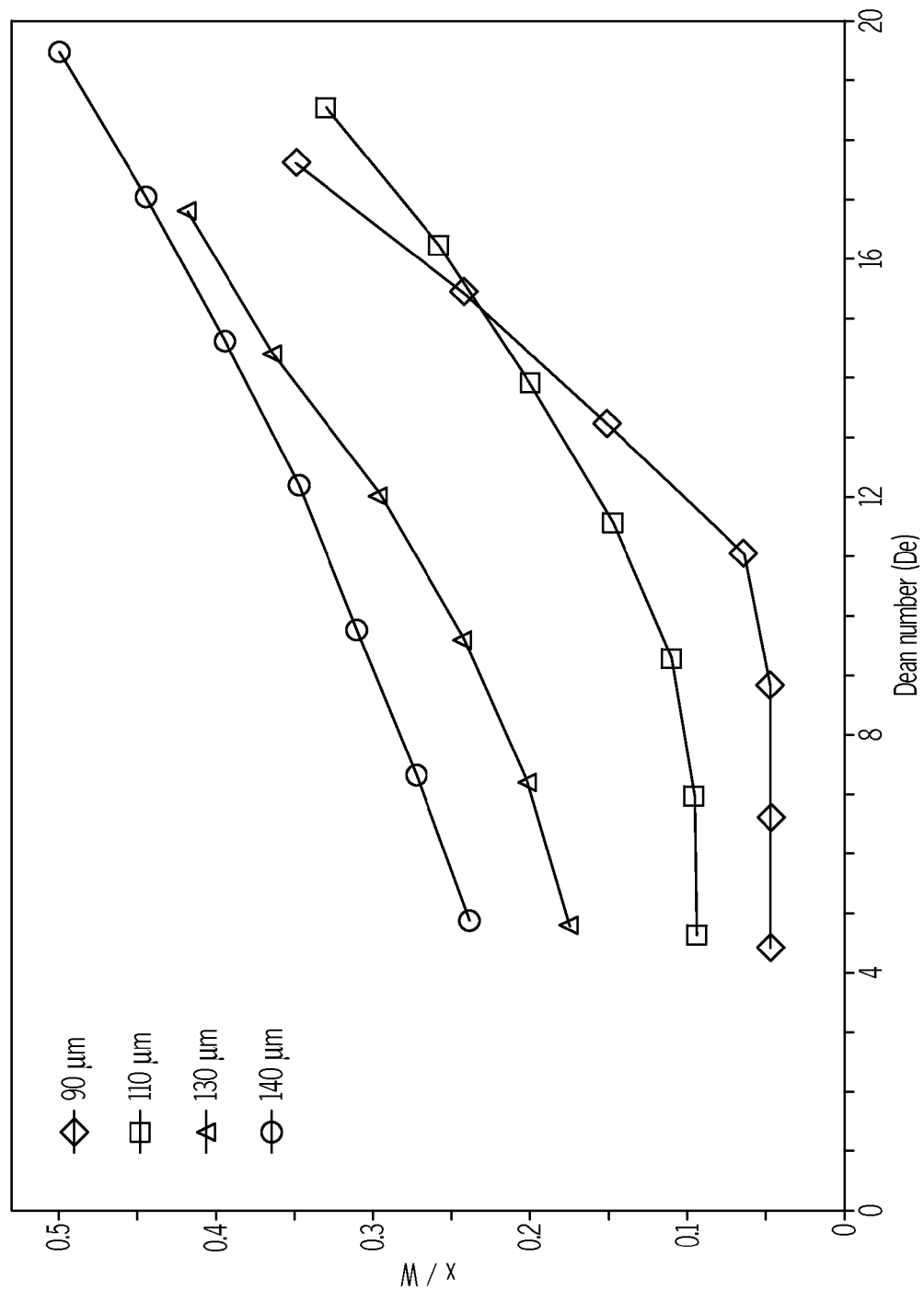
FIGS. 11A-11C graphically depict positions of 10 µm, 15 µm, and 20 µm diameter particle streams, respectively, from an inner channel wall for increasing De in microchannels ranging from 90 µm to 140 µm in height according to one or more embodiments described and illustrated herein.
Figure 11B:
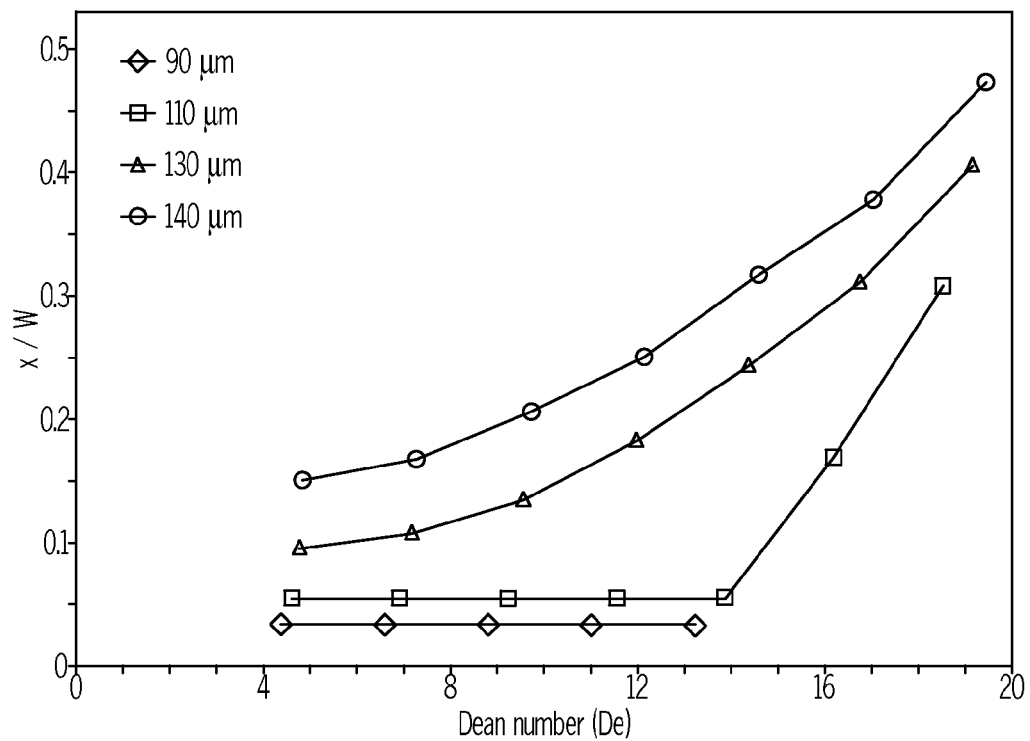
Figure 11C:
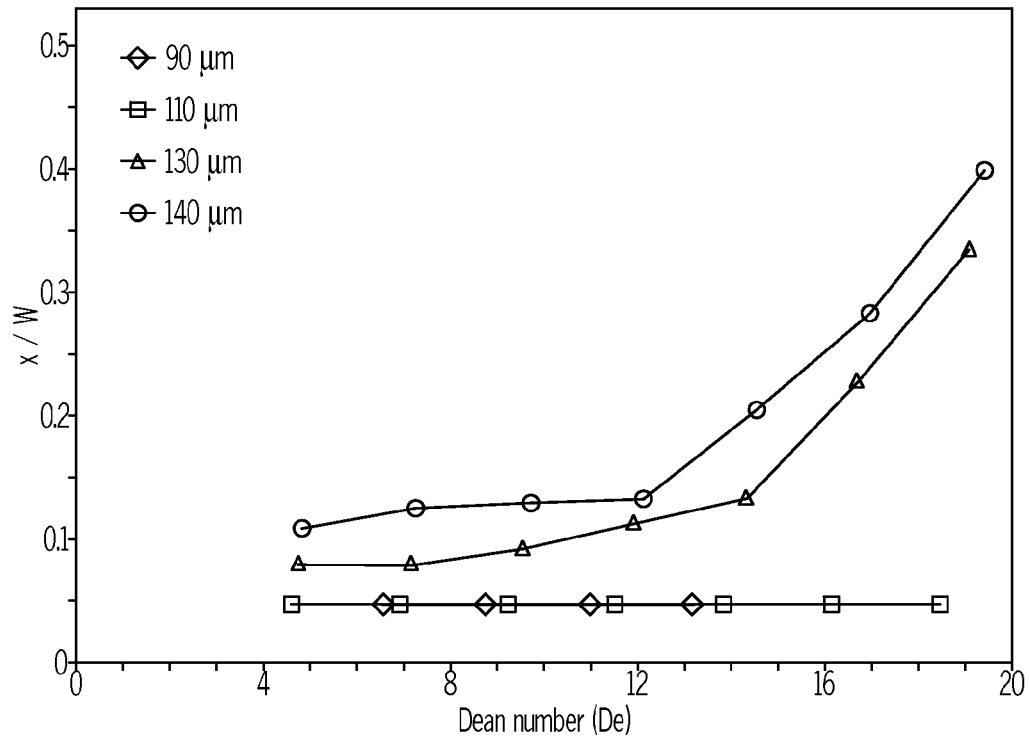

FIGS. 11A-11C plot the position of particle streams inside microchannels of different height as a function of De for 10 μm, 15 μm, and 20 μm diameter particles, respectively. For a 10 μm diameter particle in a 90 μm high channel ($a_p/H$~0.11), the distance of the particle stream from the inner microchannel wall 212 remained constant up to De=8.8 before rising linearly. The lift force acting on the particle below De=8.8 was very much greater than $F_D$ and hence the particle stream was unaffected by an increase in the fluid velocity. However, beyond a critical De (flow rate), $F_D$ increases to the same order as $F_L$, and hence the particle stream position varied linearly with the flow rate indicating a dominance of Dean drag. Increasing microchannel height reduced the critical De for particle stream migration, as seen in FIG. 11A, due to a larger Dean force with increase in channel height. Hence, in the case of 130 μm and 140 μm high microchannels ($a_p/H$~0.07), the particle stream position varied for all flow conditions tested.

For the larger 15 μm diameter particles, the higher $a_p/H$ ratio in the case of the 90 μm and 110 μm microchannels resulted in a larger lift force and hence the particle stream positions remained predominantly constant for increasing De. However, similar to the 10 μm diameter particles, an increase in channel height resulted in a lower $a_p/H$~0.1 ratio and hence the position of the particle stream was strongly influenced by the Dean force. Similarly, the 20 μm diameter particles yielded higher $a_p/H$, resulting in significant $F_L$ acting on particles in each of the channel heights considered. Hence, a prominent flat (constant position) region was observed in all plots for the 20 μm diameter particles. The increased dominance of the lift force in the case of the larger particles is primarily due to the strong dependence of the lift force on the particle diameter ($F_L \propto a_p^4$ vs. $F_D \propto a_p$). Thus, in the 90 μm channel, the 20 μm diameter particle stream position was constant for almost all flows tested.

Results from these individual particle tests indicate that a complete separation between the three particle sizes can be achieved in microchannels of different heights and a range of flow conditions.

As an example and not a limitation, to demonstrate particle separation of three particle sizes, a homogenous mixture of 10 μm, 15 μm, and 20 μm diameter polystyrene particles was introduced into a spiral microchannel particle separator as illustrated in FIG. 8A. The spiral microchannel particle separator device comprised a five loop Archimedean spiral microchannel with two inlets and eight equally spaced outlets. The spiral designs had an initial radius of curvature of 1 cm, with spacing between the successive spiral loops fixed at 500 μm. The width of the microchannel devices was fixed at 500 μm, while microchannel height was varied from 90 μm to 140 μm. At the outlet, the 500 μm wide channel opened into a 1 mm wide segment to increase spacing between particle streams before splitting into eight 100 μm wide outlets.

Particle separation was experimentally observed by using 10 μm, 15 μm, and 20 μm diameter particles labeled with DAPI, FITC and TRITC fluorophores. Corresponding filter cubes were used to capture images of each of the particle streams at the microchannel outlets. FIGS. 12A-12C schematically illustrate the captured images that were superimposed to create a composite image showing the three particle streams at the inlet, the 5$^{th}$ loop, and the outlet, respectively. To extract the three individual particle streams, the mixture was tested using the 130 μm high spiral microchannel at De=14.4 (flow rate~3 mL/min). The 500 μm wide channel opened into a 1 mm wide section 207 prior to the outlet to achieve better separation by taking advantage of the laminar flow profiles in the outlet channels.

The schematic illustrations of FIGS. 12B and 12C image indicate the formation of three distinct particle streams 217, 218, and 219 at the microchannel outlet. The position of the 10 μm particle stream 219, the 15 μm particle stream 218, and the 20 μm particle stream 217 in the 500 μm wide section 207 of the microchannel were 180 µm, 120 µm, and 65 µm respectively from the inner microchannel wall 212. Thus, particles of the three streams 217, 218, and 219 were collected at the first, second, and third outlets 206a-c, respectively. Although the microchannel height determines whether the particles focus into a single stream, it is the microchannel width that greatly influences the spacing between individual particle streams. Thus, wider channels result in larger spacing between particle streams, which in turn permits separation of particles with closely spaced diameters.

The particle streams 217, 218, and 219 from each of the eight outlets were collected in separate vials and a flow cytometry analysis was performed to quantify the separation efficiency. FIG. 13 presents the cytometry counting results using a particle detector illustrating particle distribution across the first four outlet of the spiral microchannel particle separator. Nearly 98% of the particles were filtered out at outlets 206a, 206b and 206c suggesting a high degree of particle focusing. Separation efficiency of ~90% was observed between the three particles. Even higher separation efficiencies may be achieved by using mixtures of monodispersed particles. Although only separation of three particles sizes has been described herein, a larger number of particle sizes can be simultaneously separated by using wider spiral microchannels to increase spacing between the multiple focused particles streams.

Figure 14:
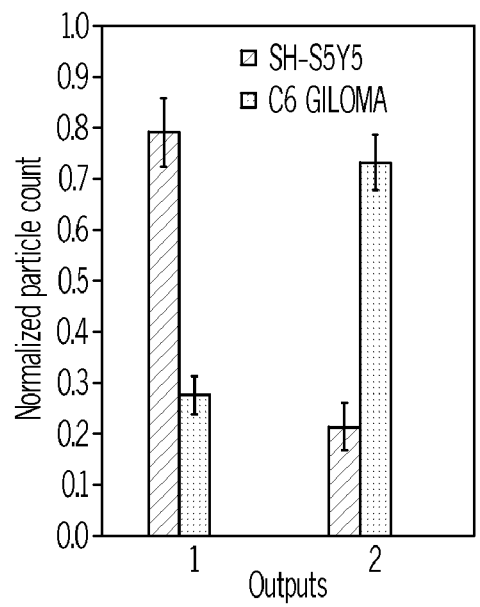
FIG. 14 graphically depicts cell counting results in a spiral microchannel particle separator according to one or more embodiments described and illustrated herein.

As an example and not a limitation, separation of cells was also achieved using the device described with respect to the example described above. The application of the developed technique to high-throughput cell sorting was demonstrated by separation of SH-SY5Y neuroblastoma and C6 glioma cells. It is noted that complete separation of these neural stem cells may be of importance to understanding the specific and unique functions these cells play in the central nervous system (CNS), and potential applications in cell replacement therapy in many neurodegenerative disorders (such as Parkinson's, Alzheimer's, or Multiple sclerosis) and cancer. Based on the size of these cells, the mixture was passed through a 120 µm high microchannel at De=11.8 to collect the bigger ~15 µm diameter cells from outlet 206a and the smaller ~8 µm diameter cells from outlet 206b. The inlet solution consisted of the two cell mixture with equal cell concentrations (~500,000×2cells/mL). Nearly 90% of the cells were collected at outlets 1 and 2, indicating a high degree of cell focusing. FIG. 14 shows the cell counting results indication ~80% separation efficiency between the two cell types, with the SH-SY5Y cells collected at first outlet 206a and the C6 glioma cells at second outlet 206b. A potential concern when separating cells is the possibility of damage to the cells due to the high shear forces. Cell viability following separation was confirmed by bringing both SH-SY5Y neuroblastoma and C6 glioma cells back into culture using the procedure described in the methods section with >90% cell recovery after 24 hrs.

Accordingly, due to the inertial and Dean drag forces acting on the particles increase with increasing flow rates, embodiments of the multiple-outlet spiral microchannel particle separators may be ideal for achieving high throughput separations. For the flow rates tested (in the mL/min range), a sorting rate of ~1 million cells/min may be achieved.

Referring now to FIG. 15, another embodiment of a particle separator device is illustrated. FIG. 15 schematically depicts a straight microchannel particle separator 400 generally comprising an inlet 402, a straight rectangular microchannel 404, a central outlet 406c, and two side outlets 406a/406b. As described in detail below, embodiments of the straight microchannel particle separator 400 may be utilized to completely or nearly completely separate particles from a solution.

In the illustrated embodiment, the inlet 402 is in fluid communication with a wide inlet segment 403 that is in fluid communication with the straight rectangular microchannel 404. The fluid inlet 402 is configured to be coupled to a solution source, such as a syringe, to receive particle-laden solution. As described in more detail below, the straight rectangular microchannel 404 comprises a high aspect ratio of height to width to focus particles of a desired size as the flow toward the three outlets 406a-c. Particles are then collected at the two side outlets 402a and 402b, while substantially-free particle solution exits the straight microchannel particle separator 400 through the center outlet 406c. The three outlets 402a-c may be fluidly coupled with solution collection devices (not shown).

Figure 16A:
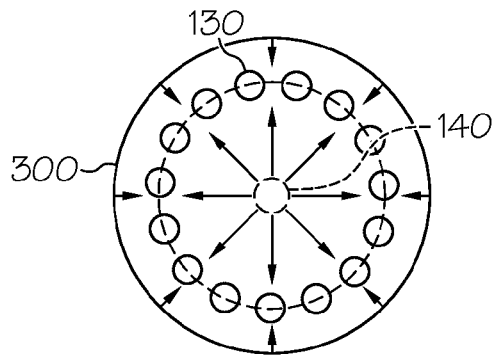
FIGS. 16A-16C schematically depict particle migration in circular, square, and rectangular cross-section channels, respectively.
Figure 16B:
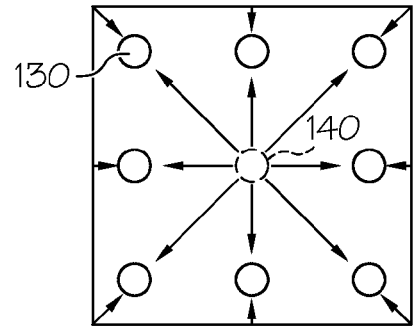
Figure 16C:
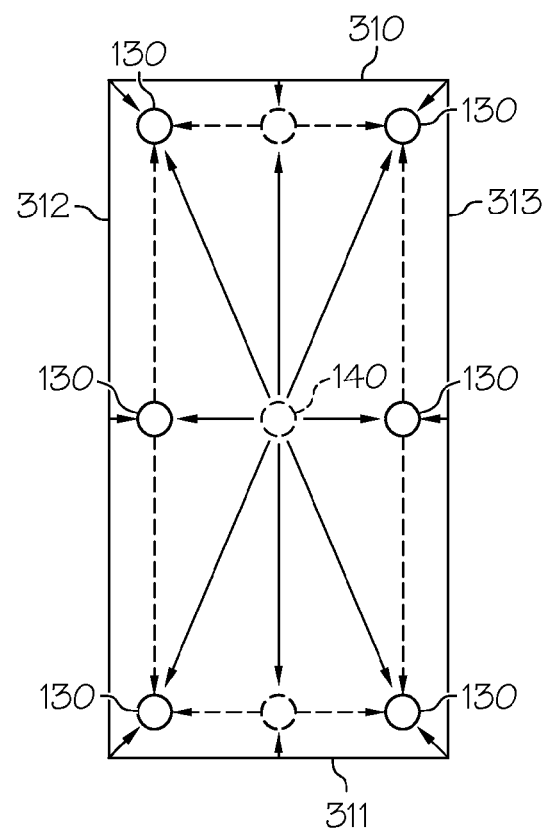

Referring to FIGS. 16A-16C, principles of inertial migration are illustrated in a circular cross-section channel, a square cross-section channel, and a rectangular cross-section channel, respectively. Neutrally buoyant particles suspended in a fluid flowing through a microchannel are subjected to both viscous drag forces and inertial lift forces. The drag forces, primarily due to the viscous nature of the carrier fluid, are responsible for entraining particles along the flow streamlines. The inertial lift forces are responsible for the lateral migration of particles 130 across the flow streamlines. The parabolic nature of the laminar velocity profile in Poiseuille flow produces a shear-induced inertial lift force that drives particles away from the microchannel center towards microchannel walls. As particles migrate closer to the channel walls, an asymmetric wake induced around particles generates a wall-induced lift force driving these particles away from the walls. In FIGS. 16A-16C, the randomly dispersed particles align to form a narrow band within the microchannel where the lift forces balance each other (illustrated by the dotted lines). The arrows indicate a direction of migration. As may be seen in FIGS. 16A-16C, particles 130 migrate from a center location 140 toward the walls of the channel. The solid circles 130 indicate final particle equilibration positions for Re≧100 flows.

Referring to FIG. 16A, particles that are uniformly dispersed in a solution migrate to form a narrow band near channel walls in a circular microchannel 300. The opposing lift forces ($F_{IL}$, and $F_{WL}$) are dependent on the particle diameter to channel diameter ratio ($a_p/D$), and dominate for $a_p/D \geq 0.07$ causing particles to equilibrate ~0.2D away from channel walls. Since the average shear rate experienced by larger particles is greater, increasing the $a_p/D$ ratio accelerates particle migration from the tube center 140 towards the circumference. It may be shown that the equilibrium position 130 shifts towards the wall for faster flows, and heavier particles also equilibrate in the same position as the neutrally buoyant particles.

Referring to FIG. 16B, for a non-circular, square microchannel cross-section channel 310, the microchannel hydraulic diameter, given by $D_h=2hw/(h+w)$ for an h high and w wide channel, can be used. Apart from the lift forces, the Dean drag forces due to the curvilinear channel geometries were employed for particle filtration application. At low Reynolds number flows (Re<100), eight stable equilibrium positions 130 exist in a square microchannel due to a uniform shear gradient on all four sides. Increasing to Re>500 reduces these equilibrium positions to four, causing all particles to equilibrate at channel corners. Although with only four corner equilibrium positions it is easy to filter and separate particles in planar microfluidic devices, high pressure drops resulting from the fast flows make this approach impractical for most microfluidic applications.

Embodiments overcome this problem of high pressure drops by modulating shear rate in the microchannels. FIG. 16C illustrates a straight rectangular microchannel having a rectangular cross-section 320 according to one embodiment. The microchannel has two first walls 312 and 313 of equal length and two second walls 310 and 311 of equal length. The two first walls 312, 313 may define a height and the two second walls 310, 311 may define a width of the rectangular cross-section 320, wherein the height is greater than the width to provide a high aspect ratio. Use of a rectangular microchannel cross-section 130 (planar Poiseuille flow) yields a higher shear rate along the narrowest dimension of the channel. In channels with high aspect ratio (AR=h/w>1), the greater shear rate across the microchannel width causes particles to preferentially equilibrate along the microchannel height, as shown by the migration of particles from locations 140, 142a and 142b to equilibrium positions 130, thus creating a central region completely devoid of particles. The larger lift forces along the narrowest dimension also reduce the channel length required for particles to undergo equilibration, and thus can be advantageous in many microfluidic applications requiring particle filtration in short distances.

Referring again to FIG. 15, the uniformly dispersed particle mixture 420 at the inlet equilibrates into two focused streams 422a and 422b near first walls 412, 410. The two focused streams of particles 422a, 422b then flow into the two side outlets 430a and 430b as illustrated by exiting streams 424a and 424b. The substantially particle-free solution flows through the central outlet. By designing appropriate outlets, particle filtration can be achieved at low Re (Re<50).

Referring to Eq. (4) above, the sign of $C_L$ and hence the lift force ($F_L$) indicates direction of particle migration. A positive $C_L$ indicates particle migration away from the channel wall towards the channel center, while negative value of $C_L$ indicates migration towards the channel walls. The net lift force expression can then be rewritten as:

$$F_L = \frac{2\rho U_f^2 a_p^4}{D_h^2} \qquad (8)$$

Hydraulic diameter is traditionally assumed as the characteristic length scale of a microchannel. For square microchannels, the characteristic length scale is the channel width or height, which is also equal to the microchannel hydraulic diameter. In rectangular microchannels, however, the characteristic length ($L_C$) is the narrowest channel dimension. Thus, in a rectangular microchannel with an aspect ratio AR=2, the lift force along the channel width is 4 times greater than along the channel height due to varying shear rates, leading to higher lateral migration along the width. By taking advantage of this principle, particle filtration and extraction can be achieved at low Re and short channel length.

The flow velocity ($U_f$) at which particles focus in microchannels can be predicted using a dimensionless parameter known as the particle Reynolds number ($Re_p$) that is related to the fluid Reynolds number (Re) through the ratio of particle and channel length scale:

$$Re_p = Re\left(\frac{a_p}{L_C}\right)^2 \qquad (9)$$

Flows with higher $Re_p$ yield faster particle migration and formation of focused particle streams at each equilibrium position.

To determine the microchannel length for particles to equilibrate at a given flow rate, particle lateral migration velocity ($U_L$) and the minimum microchannel length (L) for a particle to completely migrate to its equilibrium position can be derived using Stokes' Law as:

$$U_L = \frac{F_L}{3\pi\mu a_p} = \frac{2\rho U_f^2 a_p^3}{3\pi\mu L_C^2} \qquad (10)$$

$$L = \frac{U_{max} L_p}{U_L} \qquad (11)$$

where $L_p$ is the maximum required particle migration distance approximated as $0.5 L_C$ and $U_{max}$ is the maximum flow velocity given by $U_{max} \sim 2U_f$. Rewriting Equation (6) yields:

$$L = \frac{3\pi\mu}{2\rho U_f}\left(\frac{L_C}{a_p}\right)^3 \qquad (12)$$

Thus, the microchannel length for particles to migrate to the equilibrium positions shows a strong dependence on the $a_p/L_C$ ratio. The microchannel length varies as $1/(a_p/L_C)^3$, which indicates that a small change in the particle size or the microchannel characteristic dimension can significantly impact the channel length needed for migration. The desired channel length also varies with the flow Re, but only as 1/Re (or $1/U_f$).

As an example and not a limitation, particle flows in square and rectangular microchannels were investigated for $1 \leq Re \leq 100$, which is typical for microscale flows. Combinations of particles and rectangular microchannels to yield various $a_p/L_C$ ratios were tested. The results show that for particles to equilibrate in square and rectangular microchannels, two criteria should be satisfied: $a_p/L_C \geq 0.07$ and $Re_p > 0.05$. Using the proposed design principle, extraction of 590 nm diameter particles from mixture of 1.9 μm and 590 nm particles in a straight 20×50 μm² (w×h) microchannel is demonstrated. The larger 1.9 μm diameter particles equilibrate to form two particle streams near each sidewall and are removed using a 3-outlet system. The smaller 590 nm diameter particles remain unfocused and are extracted in the center of the 3-outlet system. Microchannels for filtration of particles of any size, including nanoparticles, can now be designed for passive continuous operation.

To illustrate particle migration, straight microchannels of varying cross-sections were fabricated and tested. Provided below are several examples that are intended to be used for illustrative purposes and not a limitations. Each straight microchannel design comprised a 4-cm long microchannel with a single inlet and three bifurcating outlets (see FIG. 15). 10 μm and 20 μm wide microchannels opened into a 100 μm and 200 μm wide sections respectively at the outlet for enhanced visualization. The microchannels were fabricated in PDMS using standard soft lithography methods. Briefly, a layer of SU-8 photoresist (2075, Microchem Corp.) was patterned on a single-side polished 3" silicon wafer using conventional photolithography techniques. The height of the microchannels was determined by the thickness of the SU-8 layer. PDMS prepolymer (Dow Corning) mixed in a 10:1 ratio with the curing agent was cast on the SU-8 master to replicate microchannel features. Following curing, the PDMS molds were peeled from the SU-8 master and bonded to a 1 mm thick glass slide using a corona surface treater (Electro-Technic Products Inc.) to complete each microchannel.

The fabricated straight microchannel devices were tested using a Plexiglas interconnect for quick and reusable microfluidic connections. Fluorescently-labeled polystyrene particles (Bangs Laboratories) dispersed in DI water (0.05% volume fraction) were pumped with a syringe pump (NE-1000X, New Era Pump Systems) at flow rates corresponding to $Re_p=0.001-10$. The density of the polystyrene particle was 1050 kg/m$^3$, yielding a particle to fluid density ratio of 1.05. To visualize particle migration, high-speed images of the microchannel were captured at the outlet using an inverted epi-fluorescence microscope (Olympus IX71) equipped with a 12-bit CCD camera (Retiga EXi, QImaging) detector device. A set of 100 images was then overlaid to create each averaged composite image. To analyze particle distribution within the microchannels, grayscale linescans across microchannel width of the composite images were recorded using ImageJ®. The fluorescent peaks from line-scans were then used to determine the position of the focused particle streams. To demonstrate extraction of particles, a mixture of 590 nm and 1.9 µm diameter polystyrene particles labeled with Dragon green (FITC) or Plum purple (DAPI) fluorophores were used.

Figure 17A:
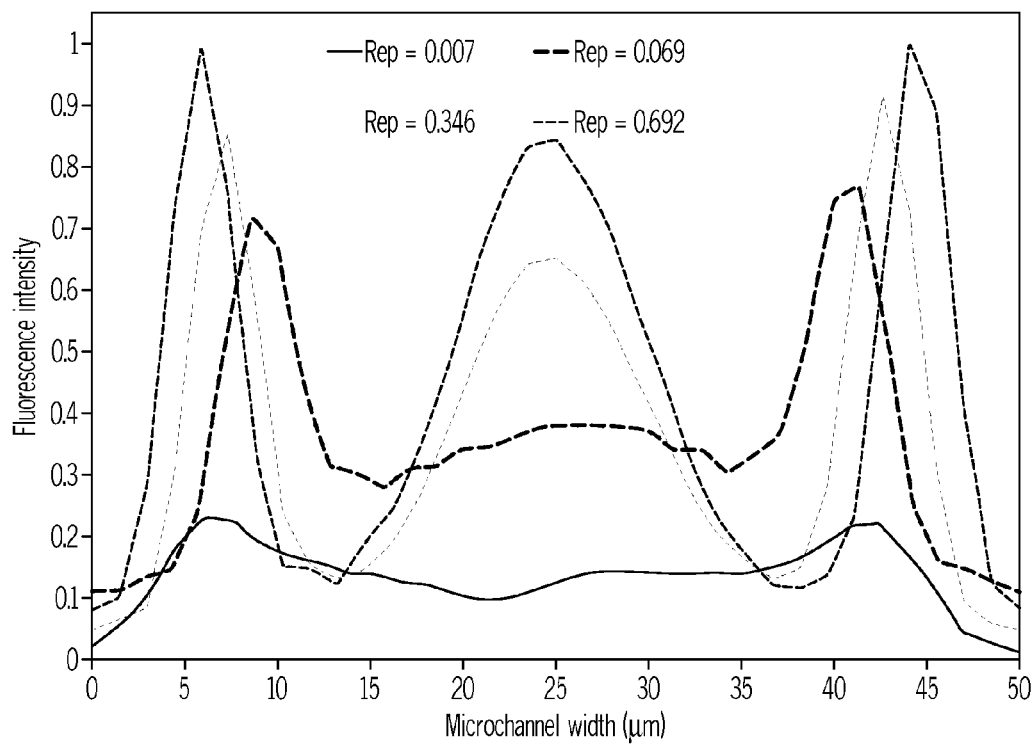
FIG. 17A graphically depicts distribution of 4.16 µm diameter particles across a width of a 50×50 µm$^2$ straight microchannel according to one or more embodiments described and illustrated herein.

As a nonlimiting as example, particle migration in square microchannels was demonstrated using 4.16 µm diameter polystyrene particles in 50×50 µm$^2$ microchannels ($D_h$=50 µm) at flow rates $0.007 \leq Re_p \leq 0.692$. The particle size to critical channel dimension ratio in this case was $a_p/L_C \sim 0.08$. At the input, particles were randomly distributed across the microchannel. FIG. 17A illustrates the distribution of 4.16 µm diameter particles across the width of a 50×50 µm$^2$ microchannel at increasing $Re_p$. For $Re_p=0.007$ (Re=1), at the outlet the particles remain evenly distributed across the microchannel cross-section indicating little migration. Increasing the flow rate to $Re_p=0.069$ (Re=10) increases the lift force which permits particles to overcome the viscous drag. At this flow rate particles begin migrating across the microchannel cross-section towards equilibrium positions and form focused streams ~$0.2L_C$ from the channel walls. For $Re_p=0.069$, the microchannel length required for particles to migrate across the 25-µm microchannel half-width for complete equilibration is ~4.1 cm. Thus not all particles equilibrate at the outlet since microchannels in this work were only 4 cm long. Increasing the flow rate to $Re_p \geq 0.346$ (Re≥50) reduces the required microchannel length to ~1 cm, resulting in full particle equilibration.

Diffusing of particles limit their focusing in these microchannels. Brownian diffusion can cause particles to cross streamlines and remain unfocused. However, Brownian diffusion is typically dominant for small particles (~200 nm) at low Re flows, while focusing of microparticles using the embodiments described herein was typically achieved for Re>10 flows, indicating the absence of Brownian diffusion. Alternatively, shear-induced diffusion due hydrodynamic particle-particle interactions can result in a diffusion-like migration of larger particles across flow streamlines. However, since the particle concentrations tested were very low (~0.05% volume fraction), shear-induced diffusion arising from particle-particle interaction should be minimal.

Figure 17B:
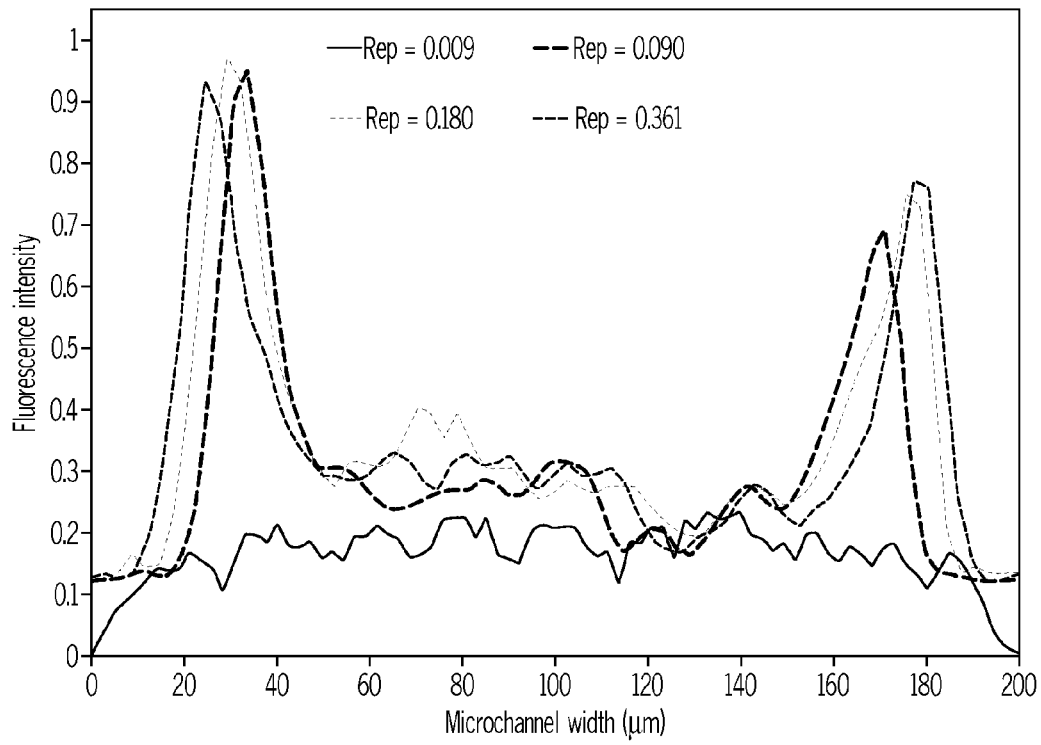
FIG. 17B graphically depicts distribution of 1.9 µm diameter particles across a width of a 20×20 µm$^2$ straight microchannel according to one or more embodiments described and illustrated herein.

Similarly, 1.9 µm diameter polystyrene particles were tested in 20×20 µm$^2$ microchannels ($a_p/L_C \sim 0.1$) at flow rates $0.009 \leq Re_p \leq 0.361$. FIG. 17B illustrates the distribution of 1.9 µm diameter particles across the width of a 20×20 µm$^2$ microchannel at increasing $Re_p$. Since 20 µm wide microchannels could not be imaged well with a 63× objective, the microchannels were fabricated to open into a 200 µm wide section at the outlet. This widening of the microchannel preserved the flow streamlines and simply amplified spacing between particles, thus permitting enhanced visualization. The small microchannel cross-section limited the testing to Re≤40 flows due to very high pressure drops (>10 MPa) along the 4 cm channel length. For $Re_p=0.009$, particles remain evenly distributed at the outlet indicating little migration. Increasing flow to $Re_p>0.05$ causes particles to form a band around the microchannel perimeter ~$0.2L_C$ away from sidewalls. Large peaks are at the corners in FIG. 19B, due to particle focusing near the vertical sidewalls, and a uniform region at the center, due to particle focusing along the horizontal sidewalls. Peaks are located ~40 µm from sidewalls of the 200 µm wide section, which is indicative of ~4 µm position inside the 20 µm microchannel, which confirms focusing approximately $0.2L_C$ away from sidewalls.

The pressure drop in these 4 cm long 20×20 µm$^2$ microchannels is estimated to be ~4 MPa at Re=40. In cell sorting applications, high pressure drops can result in cell damage. Although the pressure drop appears to be high in the tested straight square microchannels, the shear stress exerted by the fluid is expected to be much lower. It may be shown that direct hydrodynamic shearing beyond ~150 Pa is needed to cause cell damage. The maximum flow velocity of water (µ=0.001 kg/m-s) in the tested microchannels is ~1 m/s across the 20 µm channel width, yielding a maximum shear stress on the order of 100 Pa, which is less than the reported cut-off value. As the size of cells is typically larger than the diameter of particles used in this work, the channel dimensions may be scaled accordingly, thus reducing the shear stress even further.

Migration of the particle equilibrium positions closer to the microchannel walls at higher flow rates was also observed. This is indicated by the two side peaks moving closer towards the microchannel walls, from ~10 µm to ~5 µm (e.g., from ~$0.2L_C$ to ~$0.1L_C$) in FIG. 17A as particles reach full eight-position equilibration. This was not observed in FIG. 17B because full particle equilibration was not reached.

Thus, by designing appropriate bifurcating outlets, particles may be filtered out from a mixture solution using straight microchannels with square cross-sections and incorporated into lab-on-a-chip systems. Microchannel cross-section should be scaled with particle size to achieve desirable results. For a 1 µm diameter particle, microchannels should be less than 14 µm in characteristic dimension in order to satisfy the $a_p/L_C \geq 0.07$ criterion. For 10 nm diameter particles, the microchannel cross-section should exceed 140 nm.

Figure 18A:
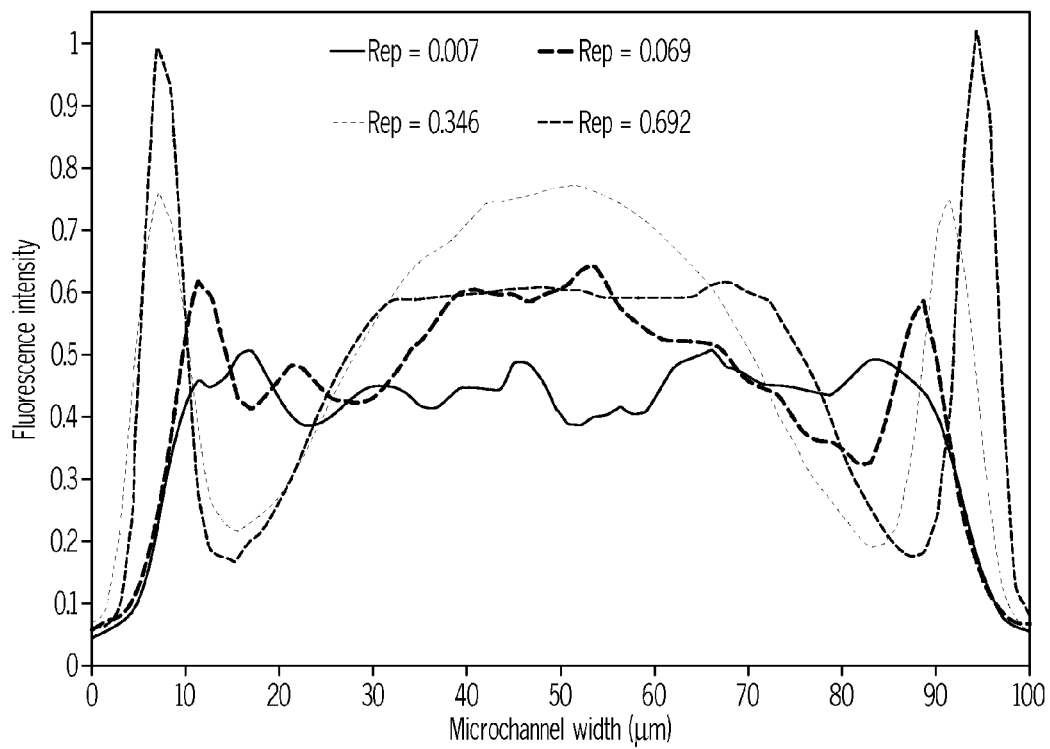
FIG. 18A graphically depicts distribution of 4.16 µm diameter particles across a width of a 100×50 µm$^2$ straight microchannel according to one or more embodiments described and illustrated herein.

In rectangular microchannels, the shear force along the microchannel perimeter is not uniform, as described above. This non-uniformity results in preferential particle focusing. In low aspect ratio microchannels (AR=h/w<1), shear rate along the channel height is higher than that along the channel width. Thus a stronger lift force is exerted on particles causing them to preferentially migrate across the microchannel height and equilibrate along the microchannel width. As an example and not a limitation, to demonstrate this phenomenon, 4.16 µm diameter particles were tested in a 100×50 µm$^2$ ($D_h$=67 µm) microchannel. FIG. 18A illustrates the distribution of 4.16 µm diameter particles across the width of a 100×50 µm$^2$ microchannel at increasing $Re_p$.

Despite the $a_p/D_h \sim 0.06$, the particles undergo equilibration since $a_p/L_C > 0.07$. At low flow rates $Re_p=0.007$, particle distribution remains uniform across the microchannel due to absence of particle equilibration (FIG. 18A). Since the lift force acting on particles along the microchannel height is four times greater than that along the width, particles begin to equilibrate along the channel width at $Re_p=0.069$. Particles remain dispersed along the microchannel width, but begin to focus along the microchannel height. Further increase in flow rate ($Re_p \geq 0.346$) causes particles to migrate and equilibrate along the microchannel width. Particles migrate outward towards the four stable corner positions, increasing the side peak intensity and decreasing intensity of the central band. As in square microchannels, side peaks move closer towards the microchannel walls at higher flowrates, from ~10 μm to ~5 μm (e.g., from ~$0.2L_C$ to ~$0.1L_C$).

Figure 18B:
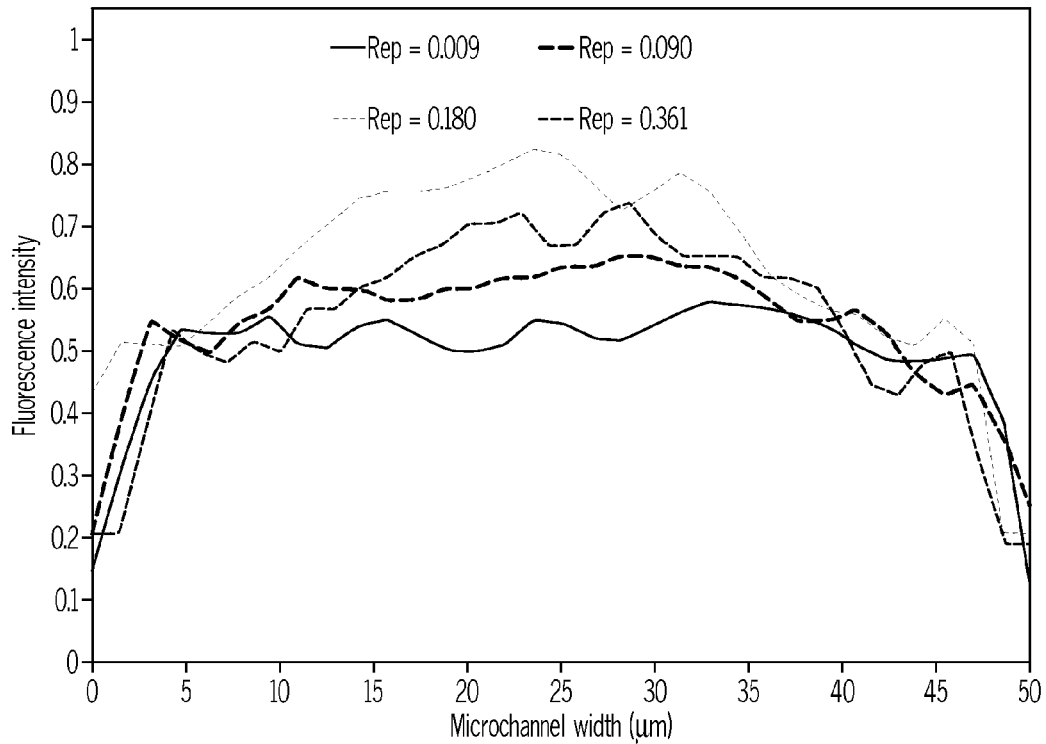
FIG. 18B graphically depicts distribution of 1.9 µm diameter particles across a width of a 50×20 µm$^2$ straight microchannel according to one or more embodiments described and illustrated herein.

Similar results were observed with 1.9 μm diameter particles in 50×20 μm² ($D_h=29$ μm) microchannel. FIG. 18B illustrates the distribution of 1.9 μm diameter particles across the width of a 50×20 μm² microchannel at increasing $Re_p$. Again particles migrate towards the wider horizontal walls, showing a uniform distribution across the channel width for all flow rates tested. However, side peaks characteristic of full equilibration are not present since faster flowrates could not be tested due to large pressure drops.

Figure 19A:
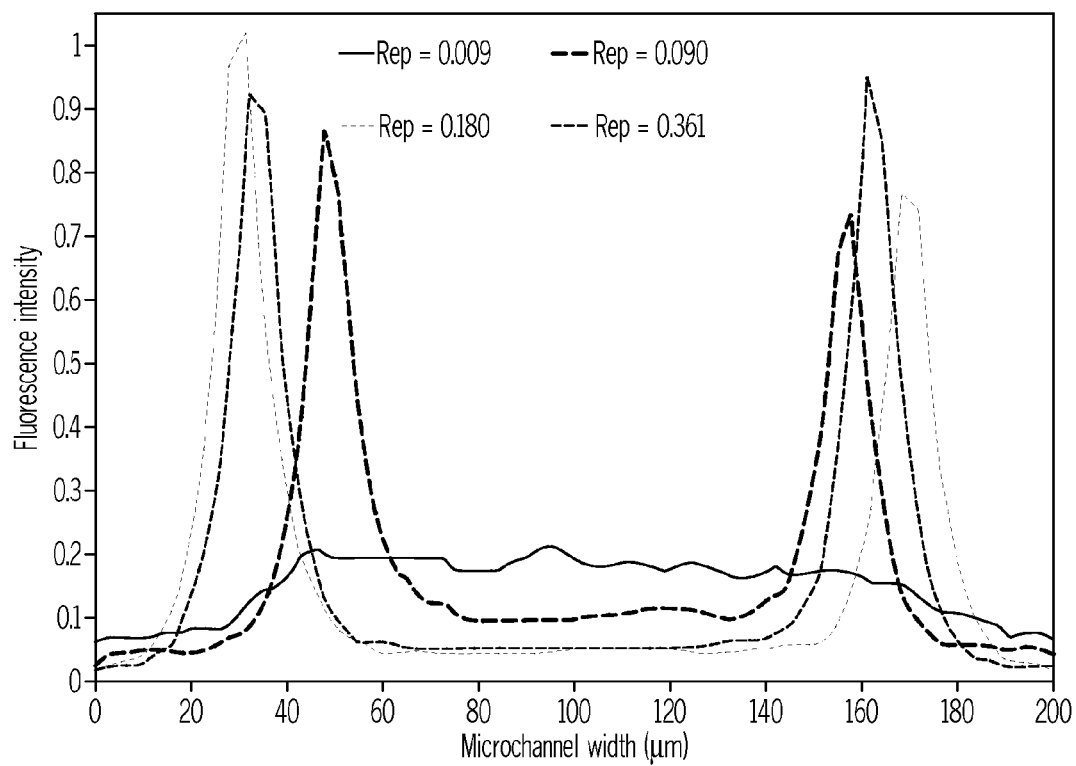
FIG. 19A graphically depicts distribution of 1.9 µm diameter particles across a width of a 20×50 µm$^2$ straight microchannel according to one or more embodiments described and illustrated herein.

Using high aspect ratio rectangular microchannels, (AR>1) the particles are forced to equilibrate along the microchannel height due to larger lift forces acting along the width. This creates a central particle-free region across the microchannel width (see FIG. 16C). As a nonlimiting example, to demonstrate preferential particle migration, 1.9 μm diameter particles were tested in 20×50 μm² microchannels ($D_h=29$ μm, AR=2.5). FIG. 19A illustrates the distribution of 1.9 μm diameter particles across the width of a 20×50 μm² microchannel at increasing $Re_p$. Particles were observed to migrate towards the larger vertical sidewalls due to higher fluidic shear along the 20-μm wide horizontal walls. The distance between the particle streams was amplified by opening the 20-1 μm wide microchannel into a 200 μm wide segment. Thus, a complete filtration of 1.9 μm diameter particles was demonstrated at low $Re_p$ flows. Linescans confirmed that the central region was completely devoid of particles even at low $Re_p$. By employing bifurcated side outlets and taking advantage of laminar flow in the widened output section, individual particle streams can then be collected and separated from the particle-free solution in the center outlet, facilitating particle extraction and filtration (see FIG. 15).

Figure 19B:
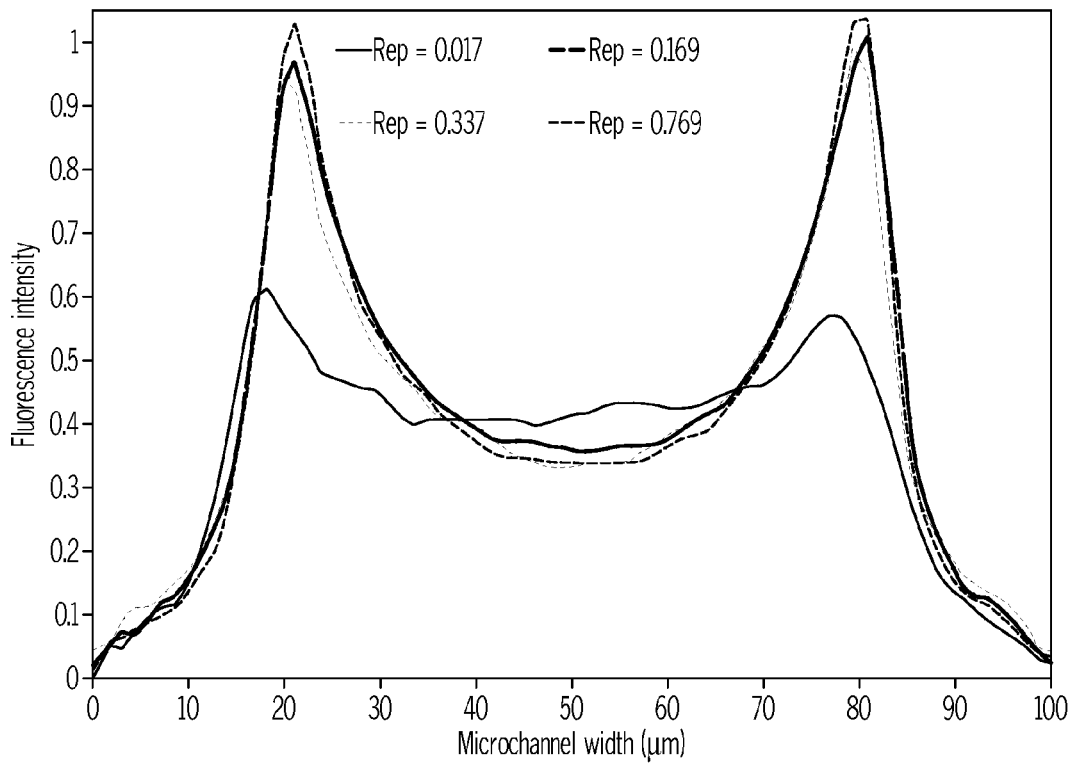
FIG. 19B graphically depicts distribution of 780 nm diameter particles across a width of a 10×20 µm$^2$ straight microchannel according to one or more embodiments described and illustrated herein.

Similar results were obtained with 780 nm diameter fluorescently labeled particles tested in 10×50 μm² microchannels (AR=5). FIG. 19B illustrates the distribution of 780 nm diameter particles across the width of a 10×50 μm² microchannel at increasing $Re_p$. The 10-1 μm wide microchannel opened into a 100-1 μm wide section at the outlet for amplifying distance between the two streams and permitting enhanced filtration. For $Re_p=0.169$, due to high shear along the 10-1 μm channel width, most of the 780 nm diameter particles equilibrated along the larger vertical channel walls. Increasing the $Re_p$ further equilibrated all particles along the channel's vertical walls in shorter distances.

As an example and not a limitation, particle extraction using shear-modulated preferential migration was demonstrated with 780 nm diameter particles in a 10×50 μm² microchannel. The individual particle streams formed ~$0.2L_C$ away from the microchannel sidewalls. By opening the 100-1 μm wide output section of the microchannel into three outlets, all particles were collected at the side outlets, with particle-free solution collected at the center outlet. Similar results were obtained using 1.9 μm diameter particles in a 20×50 μm² microchannel.

Figure 20:
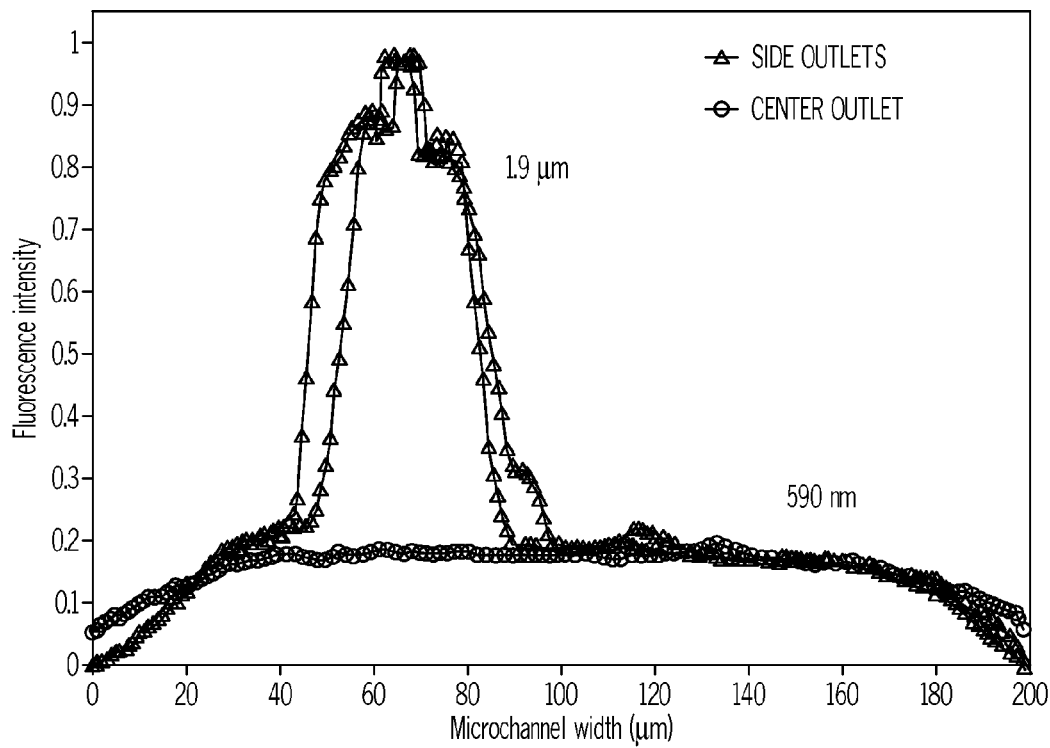
FIG. 20 graphically depicts normalized particle distribution in three outlets of a 1.9 µm and 590 nm particle mixture according to one or more embodiments described and illustrated herein.

The 20×50 μm² microchannels were used to demonstrate extraction of 590 nm diameter particles from a mixture of 1.9 μm and 590 nm particles. The 1.9 μm diameter particles equilibrated along the vertical sidewalls and were collected at the top and bottom outlets, while the 590 nm diameter particles ($a_p/L_C$~0.02) remained unfocused and were collected at the central outlet. FIG. 20 illustrates a line scan indicating the normalized particle distribution in three outlet arms of the 1.9 μm and 590 nm particle mixture. This approach can be used for size-dependent separation and purification of nanoparticles which is desirable for performing fundamental studies on their physical and chemical properties. It has been shown that the physical and chemical properties of nanoparticles are largely dependent on their size. Thus, complete filtration of potentially toxic nanoparticles using the developed method may be accomplished.

Filtration and extraction applications may require differential migration of particles of different size. To investigate conditions for particle equilibration in rectangular microchannels, a range of particle diameters ($a_p$=190 nm-9.91 μm) and channel sizes ($L_C$=10-100 μm, AR=1-10) were tested for $Re_p$=0.001-10, with the microchannel length fixed at 4 cm. As an example and not a limitation, experimental results were plotted as a function of $a_p/L_C$ and $Re_p$ in FIG. 21. The dotted line is for Re=100. Unfocused particle flows are represented by circles, partially focused particle streams are represented by squares, and focused particle streams are represented by triangles. Filled markers represent flows with Re>100.

From the experimental data and theoretical calculations, a large region for successful particle equilibration and focusing exists where $a_p/L_C$>0.07. Below this value, particles follow flow streamlines and do not experience much lateral migration, remaining unfocused at the outlet. This may be due to the drag force dominating the inertial lift force, or due to the inertial migration being too slow for complete focusing in the finite microchannel length. Another limit is seen for $Re_p$~0.05 for 4 cm long microchannels, below which inertial lift is too weak to overcome drag force for most particle sizes, and thus particles do not focus. In addition, a practical limit is seen for $a_p/L_C$>0.2, where particles begin to obstruct microchannels leading to clogging. Finally, a practical limit is also seen for Re>100, where high pressure drops result from fast flows and small channel dimensions.

For $a_p/L_C \geq 0.07$, increasing the flow rate to $Re_p$>0.05 transitions the particle flows to the inertial lift dominated region where particles undergo migration and equilibration at low Re flows, typical of most microfluidic systems. By increasing the $a_p/L_C$ ratio, particles can be focused at even lower flow rates, thus reducing pressure drop across the microchannel. Particles flowing in the high pressure dominated regime also undergo inertial migration and equilibration, but begin to equilibrate at Re>100. The data presented in FIG. 20 may be useful for determining the correct design conditions for particle equilibration depending on the particular application. For enhanced filtration and extraction of particles, one can now design appropriate microchannels and operate at flow rates such that the smaller particles fall in the viscous dominated region and the larger particles in the inertial lift dominated region.

Figure 22:
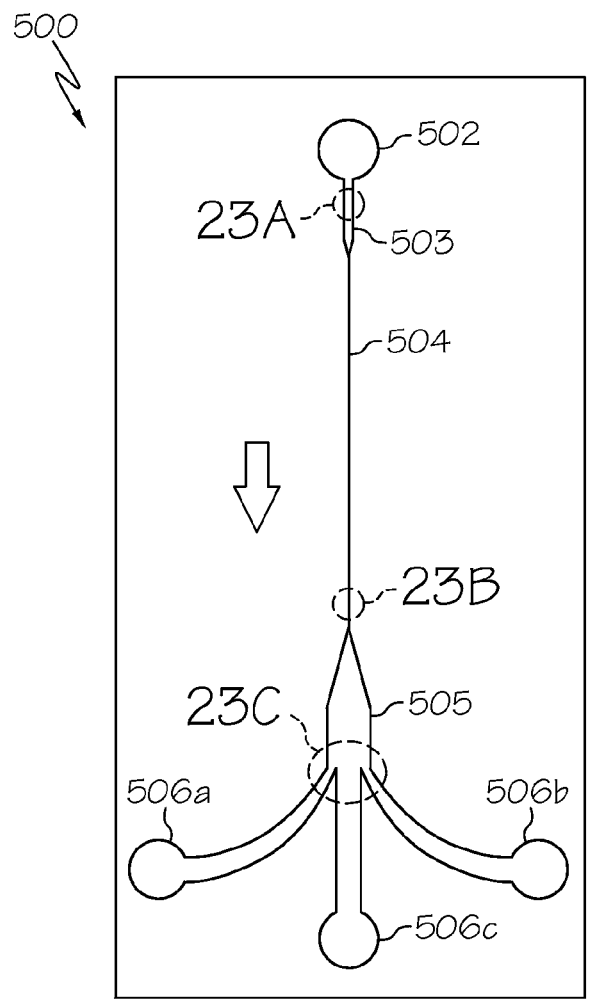
FIG. 22 schematically depicts a top view of a straight microchannel particle separator according to one or more embodiments described and illustrated herein.

Referring now to FIG. 22, a straight microchannel particle separator 500 capable of completely, or nearly completely, separating particles with a size difference as little as 2.0 μm by taking advantage of inertial focusing and diverging outlets is illustrated. More particularly, the straight microchannel particle separator 500 provides for particle filtration and extraction in rectangular microchannels by taking advantage of the asymmetric nature of microchannel cross-section to modulate the shear rate across the channel that leads to the preferential migration of particles. Using this phenomenon, two distinct particle streams can be formed at low Re, and collected downstream in individual outlets of a multiple outlet system.

Figure 21:
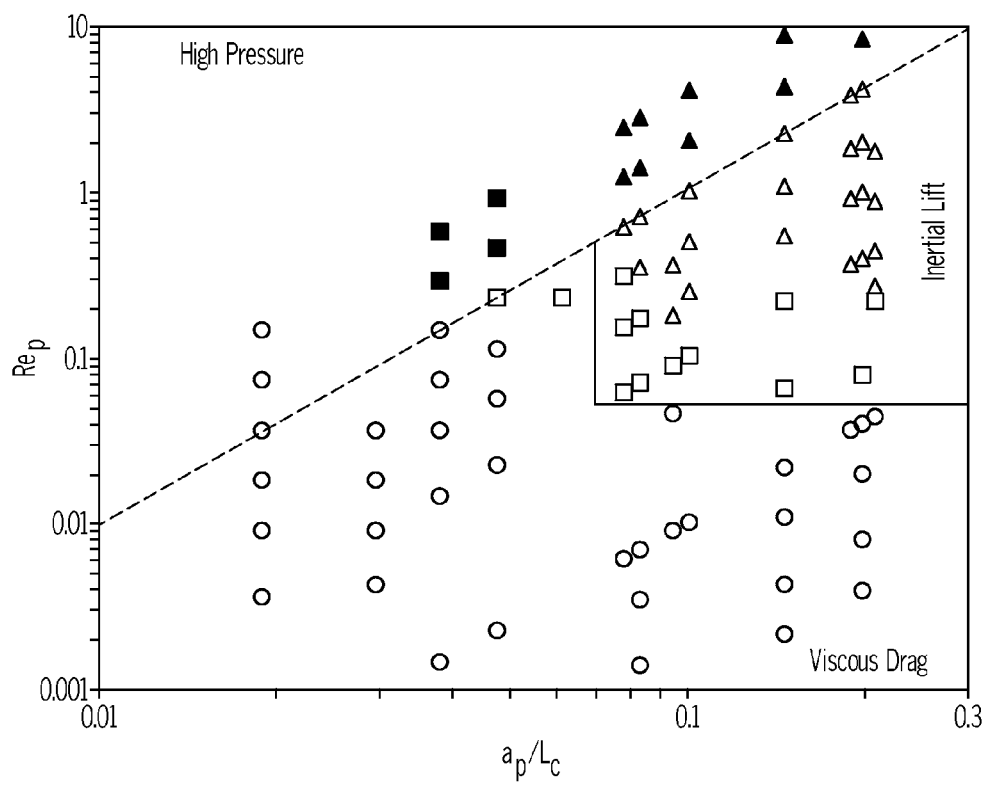
FIG. 21 graphically depicts experimental results of $Re_p$ as a function of $a_p/L_C$ according to one or more embodiments described and illustrated herein.
Figure 23A:
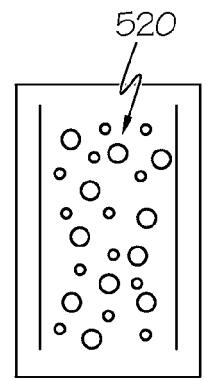
FIGS. 23A-23C schematically depict particle streams at an inlet, straight rectangular microchannel, and outlets, respectively according to one or more embodiments described and illustrated herein.

The straight microchannel particle separator 500 schematically illustrated in FIG. 21 generally comprises an inlet 502 in fluid communication with a wide inlet portion 503, a straight rectangular microchannel 504, a wide outlet portion 505, two side outlets 506a and 506b, and a center outlet 506c. FIG. 23A illustrates a solution 520 containing a homogenous mixture of two particles of two sizes flowing through the straight microchannel particle separator 500 at the wide inlet portion 503.

Figure 23B:
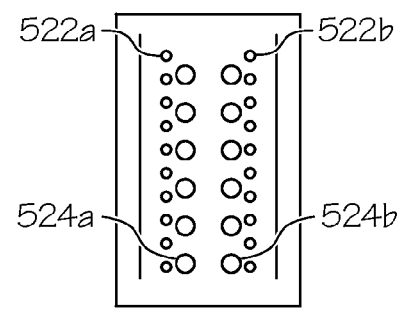
Figure 23C:
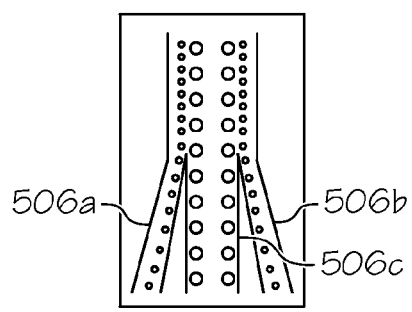

Particles or cells flowing in straight rectangular microchannel 504 experience inertial lift forces, namely shear-induced and wall-induced, as described above. As illustrated in FIGS. 23B and 23C, these forces cause the particles to equilibrate in narrow bands near channel sidewalls. Particles equilibrate when the particle diameter ($a_p$) and the critical channel dimension ($L_c$) satisfy the condition of $a_p/L_c \geqq 0.07$. Particles of different size will focus at different planes with respect to the sidewalls. Smaller particles focus closer to the sidewall as illustrated by streams 522a and 522b as compared to the larger particles as illustrated by streams 524a and 524b.

As an example and not a limitation, rectangular microchannels 15 μm×50 μm were fabricated in PDMS using standard soft lithography methods as described above. The straight rectangular microchannel opened into a wider region ranging from 100 μm to 1.5 mm wide, before the trifurcated outlet as shown in FIG. 22. Separation experiments were performed using polystyrene particles ranging from 1.0 μm to 7.32 μm in diameter (Bags Labs Inc. and Polysciences Inc.), labeled with DAPI and FITC fluorophores. Particles were introduced using a 5 cc syringe driven with a syringe pump. Flow rates in the range of 10-100 μL/min were used. Fluorescent images captured with a high-speed 12-bit CCD camera detector device were stacked to form a composite (100 images each) indicating particle stream position within the microchannel.

Figure 24:
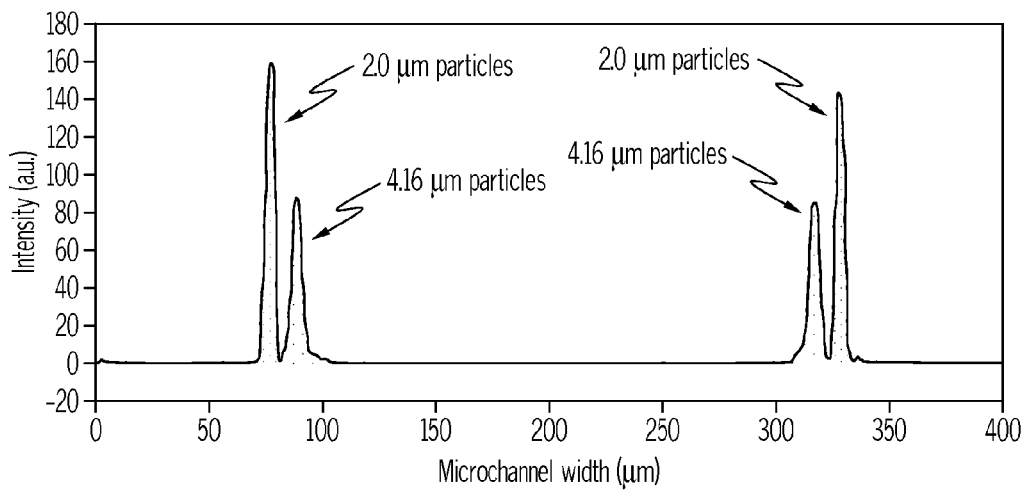
FIG. 24 graphically depicts distribution of 2 μm and 4.16 μm diameter particles in a straight rectangular microchannel according to one or more embodiments described and illustrated herein.

FIG. 24 depicts intensity line scans that illustrate distinct peaks for 2 μm and 4.16 μm diameter particles. A homogeneous mixture of randomly distributed particles at the inlet was focused in two distinct streams at the 400 μm wide outlet using a 2 cm long straight channel. Particles of different sizes were found to focus at different distances from the sidewall. There are minor various on the focused positions of particles for different outlet systems but they are approximately around the 0.2 W distance, where W is the channel width. FIG. 24 shows that as the outlet width increases, the distance between the focused stream of 2 μm and 4.16 μm particles also increases. This characteristic can be utilized for design of appropriate outlet systems to collect individual particles separately.

Figure 25:
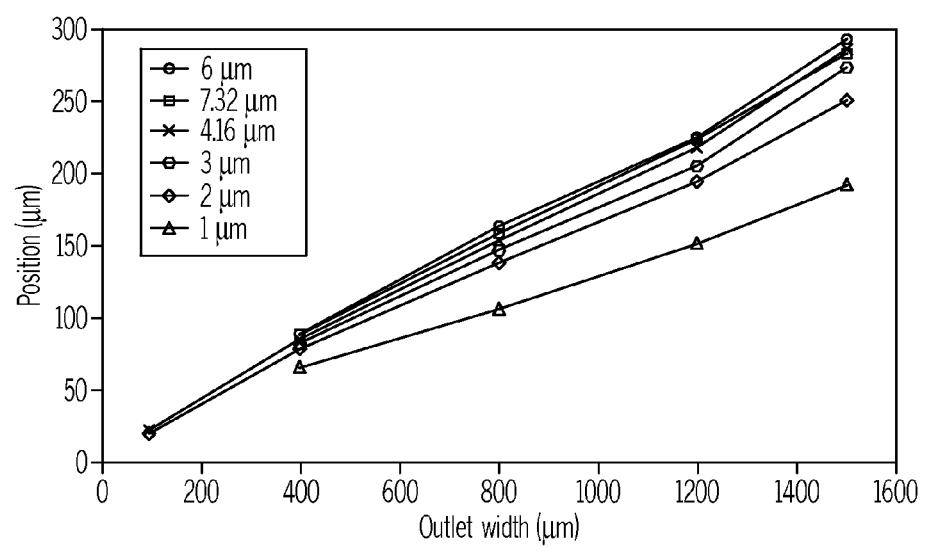
FIG. 25 graphically depicts different between focusing positions of different particles as outlet width increases according to one or more embodiments describing and illustrated herein.

It was shown that complete separation of 2 μm and 4.16 μm particles was achieved at a flow rate of 55 μt/min in a 1.25 cm long straight rectangular microchannel with a 1500 μm wide outlet. As can be seen from FIG. 25, that for particles, ranging from 1 μm to 7.32 μm, the distance between the respective focused streams increases with an increase in outlet width.

Accordingly, particles with a size difference of as little as 2 μm may be separated using a passive microfluidic device. As an example, by using a 15 μm×50 μm rectangular straight microchannel which opened out to a 1500 μm wide outlet, 2 μm and 4.16 μm particles may be separated from a homogeneous mixture. When the channel dimensions are scaled up, larger particles having small size difference can also be separated. For instance, white blood cells (10-20 μm) can be separated from red blood cells (8 μm).

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

What is claimed is:

1. A spiral microchannel particle separator comprising:
   an inlet for receiving a solution containing particles;
   a microchannel arranged in a plurality of loops, the microchannel comprising a spiral radius of curvature R, a microchannel length L, and a hydraulic diameter $D_h$; and
   at least two outlets;
   wherein:
      particles within a solution flowing through the spiral microchannel experience a lift force $F_L$ and a Dean drag force $F_D$;
      the spiral radius of curvature R and the hydraulic diameter $D_h$ of the spiral microchannel are such that for a flow rate U of the solution, the lift force $F_L$ and a Dean drag force $F_D$ are approximately equal and act in opposite directions for particles of a first size;
      the particles of the first size are focused in a single stream located at an equilibrium position near an inner wall of the microchannel; and
      the microchannel length L is such that the particles of the first size exit the spiral microchannel particle separator at a first outlet of the at least two outlets.

2. The spiral microchannel particle separator of claim 1 wherein the spiral microchannel particle separator is fabricated from poly-dimethylsiloxane, polymethylmethacrolate, polycarbonate, or cyclic olefin copolymer.

3. The spiral microchannel particle separator of claim 1 wherein particles of the first size are less than 25 μm in diameter.

4. The spiral microchannel particle separator of claim 1 wherein the flow rate U is such that a flow of the solution is characterized by a Dean number $D_e$ that is less than 1.0.

5. The spiral microchannel particle separator of claim 1 wherein the flow rate U is such that a flow of the solution is characterized by a Dean number $D_e$ equal to about 0.47.

6. The spiral microchannel particle separator of claim 1 wherein the particles of the first size are maintained at the equilibrium position by the lift force $F_L$ and the Dean drag force $F_D$.

7. The spiral microchannel particle separator of claim 1 wherein particles that are not of the first size are located at an outer half of the microchannel and exit the spiral microchannel particle separator at a second outlet of the at least two outlets.

8. The spiral microchannel particle separator of claim 1 wherein:
   the microchannel comprises:
      a width of about 100 μm;
      a height of about 50 μm;
      five loops with a spacing of 250 μm between successive loops;
   the microchannel length L is about 13 cm; and
   the spiral radius of curvature R is about 3 mm.

9. The spiral microchannel particle separator of claim 1 wherein particles that are not of the first size exit the spiral microchannel particle separator at a second outlet of the at least two outlets.

10. The spiral microchannel particle separator of claim 1 wherein:
the spiral microchannel particle separator comprises a second outlet and a third outlet;
an aspect ratio of a microchannel height to a microchannel width is such that the particles of the first size are focused in a first stream at a first equilibrium position, particles of a second size are focused in a second stream at a second equilibrium position, and particles of a third size are focused in a third stream at a third equilibrium position when the solution flows through the spiral microchannel at a Dean number $D_e$;
the lift force $F_L$ and the Dean drag force $F_D$ are approximately equal for particles of the first, second and third sizes at the first, second and third equilibrium positions, respectively; and
the particles of the first size exit the spiral microchannel particle separator at the first outlet, the particles of the second size exit the spiral microchannel particle separator at the second outlet, and the particles of the third size exit the spiral microchannel particle separator at the third outlet.

11. The spiral microchannel particle separator of claim 10 wherein:
the spiral microchannel particle separator comprises an additional outlet;
particles of an additional size are focused in an additional stream at an additional equilibrium position when the solution flows through the spiral microchannel at a Dean number $D_e$; and
particles of the additional size exit the spiral microchannel particle separator at the additional outlet.

12. The spiral microchannel particle separator of claim 10 wherein the microchannel width is about 500 µm and the microchannel height is between about 90 µm and about 140 µm.

13. The spiral microchannel particle separator of claim 10 wherein the spiral microchannel particle separator has a particle throughput of about one million particles per minute.

14. A continuous particle separator and detection system comprising:
a spiral microchannel particle separator comprising:
an inlet for receiving a solution containing particles;
a microchannel arranged in a plurality of loops, the microchannel having a spiral radius of curvature R, a microchannel length L, and a hydraulic diameter $D_h$; and
at least two outlets, wherein:
particles within a solution flowing through the spiral microchannel experience a lift force $F_L$ and a Dean drag force $F_D$;
the spiral radius of curvature R and the hydraulic diameter $D_h$ of the spiral microchannel are such that for a flow rate U of the solution, the lift force $F_L$ and a Dean drag force $F_D$ are approximately equal and act in opposite directions for particles of a first size;
the particles of the first size are focused in a single stream located at an equilibrium position near an inner wall of the microchannel; and
the microchannel length L is such that the particles of the first size exit the spiral microchannel particle separator at a first outlet of the at least two outlets;
a rigid substrate layer, wherein the spiral microchannel particle separator is bonded to the rigid substrate layer;
a particle detector for detecting particles of the first size focused in the single stream.

15. The continuous particle separator and detection system of claim 14 wherein the particle detector comprises an optical particle detector at the at least two outlets.

16. The continuous particle separator and detection system of claim 14 wherein the particles of the first size are maintained at the equilibrium position by the lift force $F_L$ and the Dean drag force $F_D$.

17. The continuous particle separator and detection system of claim 14 wherein:
the spiral microchannel particle separator comprises a second outlet and a third outlet;
an aspect ratio of a microchannel height to a microchannel width is such that the particles of the first size are focused in a first stream at a first equilibrium position, particles of a second size are focused in a second stream at a second equilibrium position, and particles of a third size are focused in a third stream at a third equilibrium position when the solution flows through the spiral microchannel at a Dean number $D_e$;
the lift force $F_L$ and the Dean drag force $F_D$ are approximately equal for particles of the first, second and third sizes at the first, second and third equilibrium positions, respectively; and
the particles of the first size exit the spiral microchannel particle separator at the first outlet, the particles of the second size exit the spiral microchannel particle separator at the second outlet, and the particles of the third size exit the spiral microchannel particle separator at the third outlet.

18. The continuous particle separator and detection system of claim 17 wherein:
the spiral microchannel particle separator comprises an additional outlet;
particles of an additional size are focused in an additional stream at an additional equilibrium position when the solution flows through the spiral microchannel at a Dean number $D_e$; and
particles of the additional size exit the spiral microchannel particle separator at the additional outlet.

* * * * *